United States Patent
Uenosono et al.

(10) Patent No.: US 9,453,832 B2
(45) Date of Patent: Sep. 27, 2016

(54) BIOLOGICAL SAMPLE MEASUREMENT DEVICE

(75) Inventors: Kaoru Uenosono, Ehime (JP); Tadashi Okada, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 371 days.

(21) Appl. No.: 14/125,452

(22) PCT Filed: Jul. 24, 2012

(86) PCT No.: PCT/JP2012/004720
§ 371 (c)(1),
(2), (4) Date: Dec. 11, 2013

(87) PCT Pub. No.: WO2013/018315
PCT Pub. Date: Feb. 7, 2013

(65) Prior Publication Data
US 2014/0123735 A1  May 8, 2014

(30) Foreign Application Priority Data

Aug. 1, 2011 (JP) .................................. 2011-168115
Sep. 29, 2011 (JP) .................................. 2011-213965
Jan. 16, 2012 (JP) .................................. 2012-005792

(51) Int. Cl.
*G01N 33/49* (2006.01)
*G01N 33/487* (2006.01)

(52) U.S. Cl.
CPC .......... *G01N 33/49* (2013.01); *G01N 33/4875* (2013.01); *G01N 33/48785* (2013.01)

(58) Field of Classification Search
CPC ........... G01N 33/49; G01N 33/48785; G01N 33/4875

USPC ........................................................ 73/61.41
See application file for complete search history.

(56) References Cited

U.S. PATENT DOCUMENTS 7,850,910 B2   12/2010   Creaven et al.
8,062,235 B2   11/2011   Planman et al.
(Continued)

FOREIGN PATENT DOCUMENTS

CN    1326547    12/2001
CN    101400985    4/2009
(Continued)

OTHER PUBLICATIONS

Japanese Office Action, Jan. 20, 2015; Japanese Application No. 2013-526740 (2 pages).
(Continued)

*Primary Examiner* — Daniel S Larkin
(74) *Attorney, Agent, or Firm* — Hamre, Schumann, Mueller & Larson, P.C.

(57) ABSTRACT

The present invention pertains to a biological sample measurement device, which is intended to be easier to use. To achieve this object, the present invention comprises a main body case (1) having a sensor insertion opening into which a sensor for measuring biological samples is inserted, a connection terminal (20) provided within the main body case (1) behind the sensor insertion opening, (5) and a shutter 7 that is provided within the main body case (1) between the sensor insertion opening (5) and the connection terminal (20) and that opens and closes the sensor insertion opening (5). This configuration makes the device easy to use.

16 Claims, 27 Drawing Sheets

(56) References Cited

U.S. PATENT DOCUMENTS

| | | |
|---|---|---|
| 2008/0099332 A1 | 5/2008 | Scott et al. |
| 2008/0200782 A1 | 8/2008 | Planman et al. |
| 2010/0128262 A1 | 5/2010 | Uehata |
| 2011/0167935 A1 | 7/2011 | Lai |
| 2012/0065544 A1 | 3/2012 | Planman et al. |
| 2012/0211360 A1 | 8/2012 | Scott et al. |

FOREIGN PATENT DOCUMENTS

| | | |
|---|---|---|
| EP | 1118856 | 7/2001 |
| JP | 01-194159 | 8/1989 |
| JP | 11-306745 | 4/1999 |
| JP | 2003-042994 | 2/2003 |
| JP | 2003-114213 | 4/2003 |
| JP | 2003-132665 | 5/2003 |
| JP | 2009-501584 | 1/2009 |
| JP | 2009-229356 | 10/2009 |
| JP | 2010-094402 | 4/2010 |
| JP | 2011-232170 | 11/2011 |
| WO | WO 2011/136306 | 11/2011 |

OTHER PUBLICATIONS

Japanese Office Action, issued in the corresponding Japanese Application No. 2013-526740, dated Aug. 18, 2015, 3 pages.
International Search Report issued in PCT/JP2012/004720, Sep. 11, 2012 (2 pages).
Extended European Search Report issued in EP Application No. 12820181.1, Oct. 10, 2014 (5 pages).
Chinese Office Action issued in CN Application No. 201280029094. 4, Oct. 24, 2014 with English translation (9 pages).

BIOLOGICAL SAMPLE MEASUREMENT DEVICE

TECHNICAL FIELD

The present invention relates to a measurement device for measuring biological information, such as a blood glucose level.

BACKGROUND ART

A conventional biological sample measurement apparatus of this kind was configured as follows.

Specifically, a conventional biological sample measurement device comprised a main body case having a sensor insertion opening, and a connection terminal provided behind the sensor insertion opening inside this main body case.

Also, a shutter that prevents the intrusion of dust through the sensor insertion opening portion is provided to the outer portion of the main body case of the sensor insertion opening (see Patent Literature 1 below, for example).

CITATION LIST

Patent Literature

Patent Literature JP2009-501584

SUMMARY

Technical Problem

However, with the prior art discussed above, since the shutter is provided on the outside of the main body case to prevent the intrusion of dust through the sensor insertion opening, when the sensor is inserted into the sensor insertion opening, the user's hand touches the shutter provided to the outside of the main body case, and this makes the job of inserting the sensor more difficult and makes the device less convenient to use.

In view of this, it is an object of the present invention to provide a biological sample measurement device that takes the problems encountered in the past into account, and with which is more convenient to use because it is easier to insert a sensor.

Solution to Problem

To achieve the stated object, the biological sample measurement device pertaining to the present invention comprises a main body case having a sensor insertion opening into which a sensor for measuring biological samples is inserted, a connection terminal provided within the main body case and behind the sensor insertion opening, and a shutter that is provided within the main body case and between the sensor insertion opening and the connection terminal and that opens and closes the sensor insertion opening.

Consequently, the job of inserting the sensor is easier, and a biological sample measurement device that is more convenient to use can be provided. Specifically, since a shutter that can open and close is provided within the main body case, the user's hand will not inadvertently touch the shutter during use, which makes the device more convenient to use. In particular, the user's hand will not touch the shutter when the sensor is being inserted into this sensor insertion opening, which makes sensor insertion easier to do.

Also, the biological sample measurement device pertaining to the present invention further comprises a sensor ejection mechanism for ejecting the sensor mounted to the connection terminal to the outside of the main body case from the sensor insertion opening, wherein the shutter is driven open by the sensor ejection mechanism during sensor ejection by the sensor ejection mechanism.

Consequently, since the shutter is configured so that it is driven open by the sensor ejection mechanism, this shutter is opened up when the sensor is ejected, and the sensor can be ejected outside of the main body case through a sensor insertion component, and this also makes the device more convenient to use.

Also, the biological sample measurement device pertaining to the present invention further comprises a shutter drive mechanism that is provided inside the main body case and that opens and closes the shutter, and a manipulation body insertion component into which a manipulation body that drives the shutter drive mechanism is inserted from outside the main body case, wherein the manipulation body insertion component has an opening formed in the surface of the main body case, and the opening is covered by a portion of the manipulation body disposed outside the main body case when the manipulation body is inserted into the manipulation body insertion component.

Consequently, when the manipulation body is inserted into the manipulation body insertion component, the opening formed in the surface of the main body case is covered by the portion of the manipulation body disposed on the outside of the main body case, so not only the sensor insertion opening, but also the manipulation body insertion component is covered, and as a result it is less likely that a disinfectant solution, water, or the like will find its way into the main body case when the main body case is washed with disinfectant solution, water, or the like.

Advantageous Effects

With the present invention, the job of inserting a sensor is easier, and a biological sample measurement device that is more convenient to use can be provided.

DESCRIPTION OF EMBODIMENTS

The biological sample measurement device in an embodiment of the present invention will now be described in detail through reference to the drawings.

Embodiment 1

Configuration of Biological Sample Measurement Device

Figure 1:
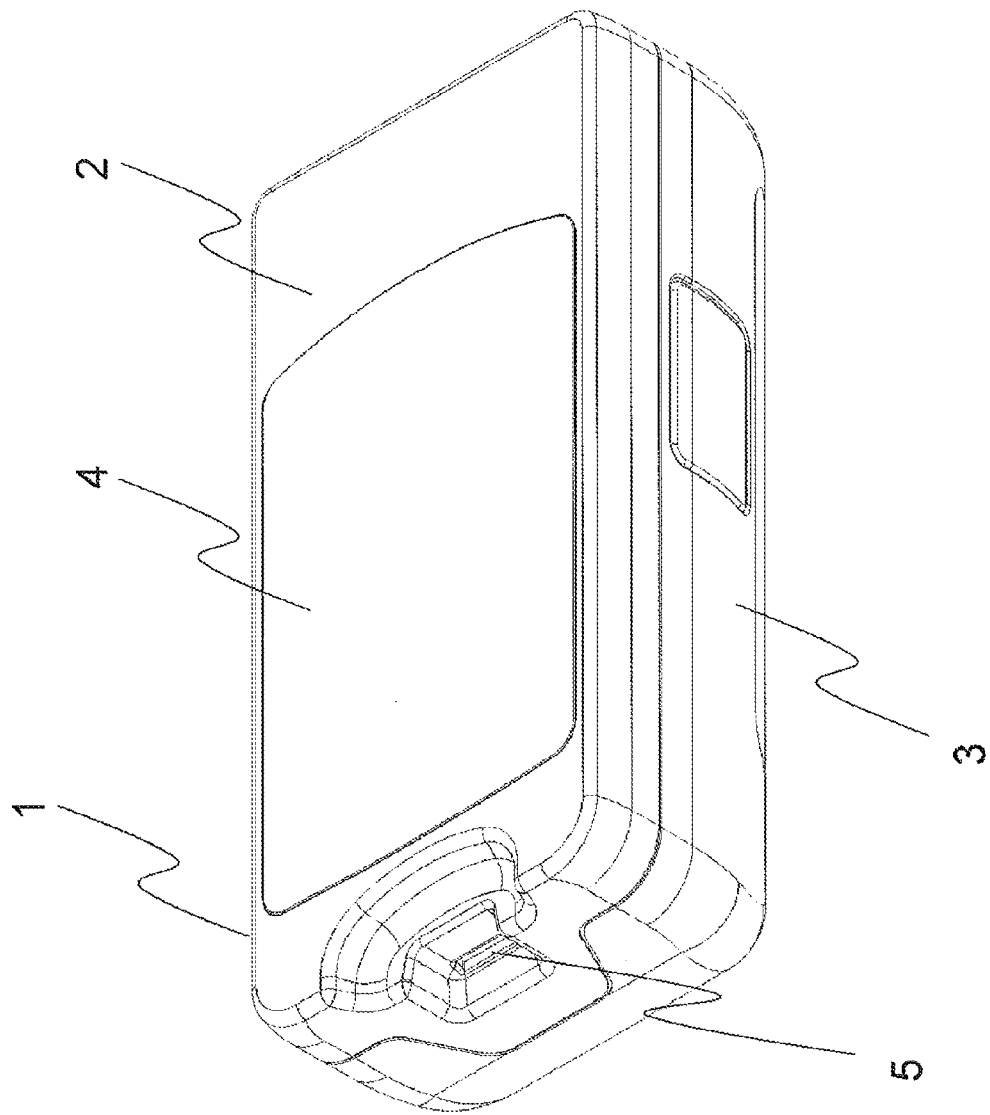
FIG. 1 is an oblique view of a biological sample measurement device in Embodiment 1 of the present invention.
Figure 2:
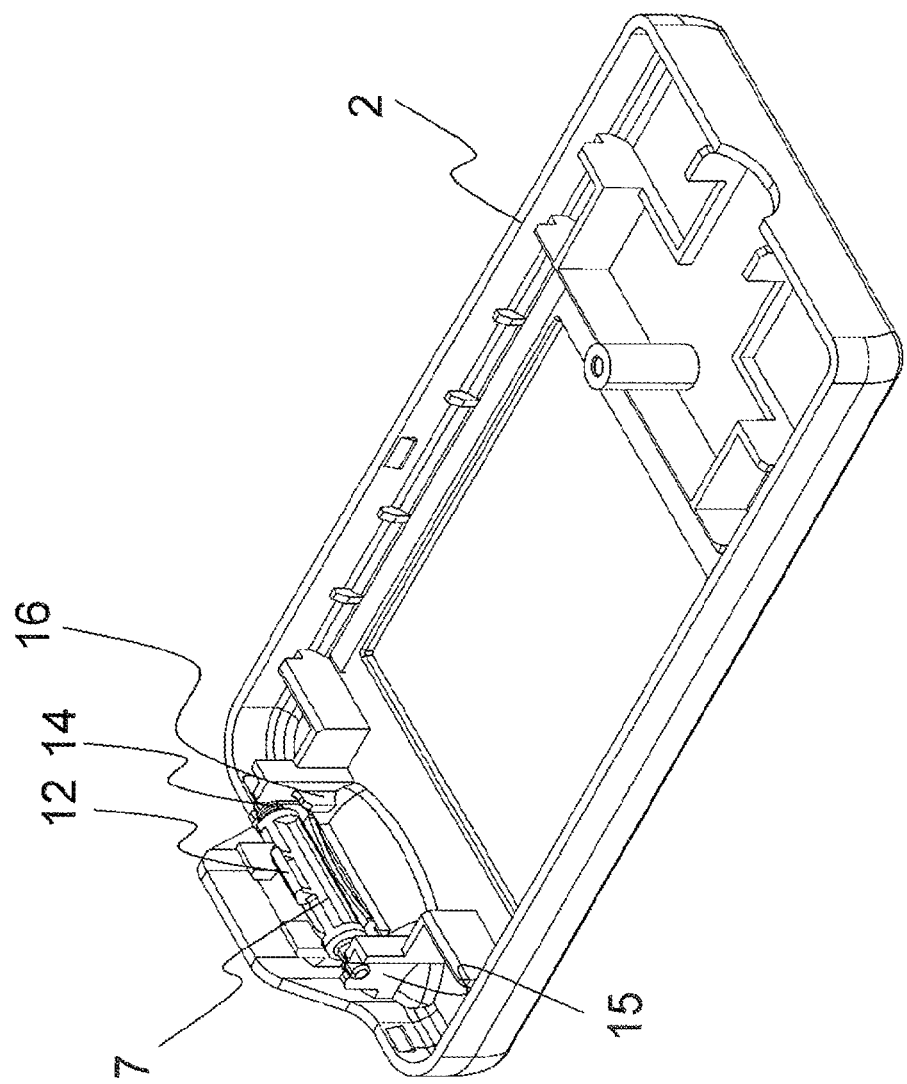
FIG. 2 is an oblique view of the lower face portion of an upper case of the biological sample measurement device in Embodiment 1 of the present invention.

In FIG. 1, 1 is a main body case with a cuboid shape. As shown in FIG. 2, this main body case 1 is constituted putting an upper case 2 that is open on the lower face side and a lower case 3 that is open on the upper face side together so that their openings are facing each other, and linking the two.

Figure 7:
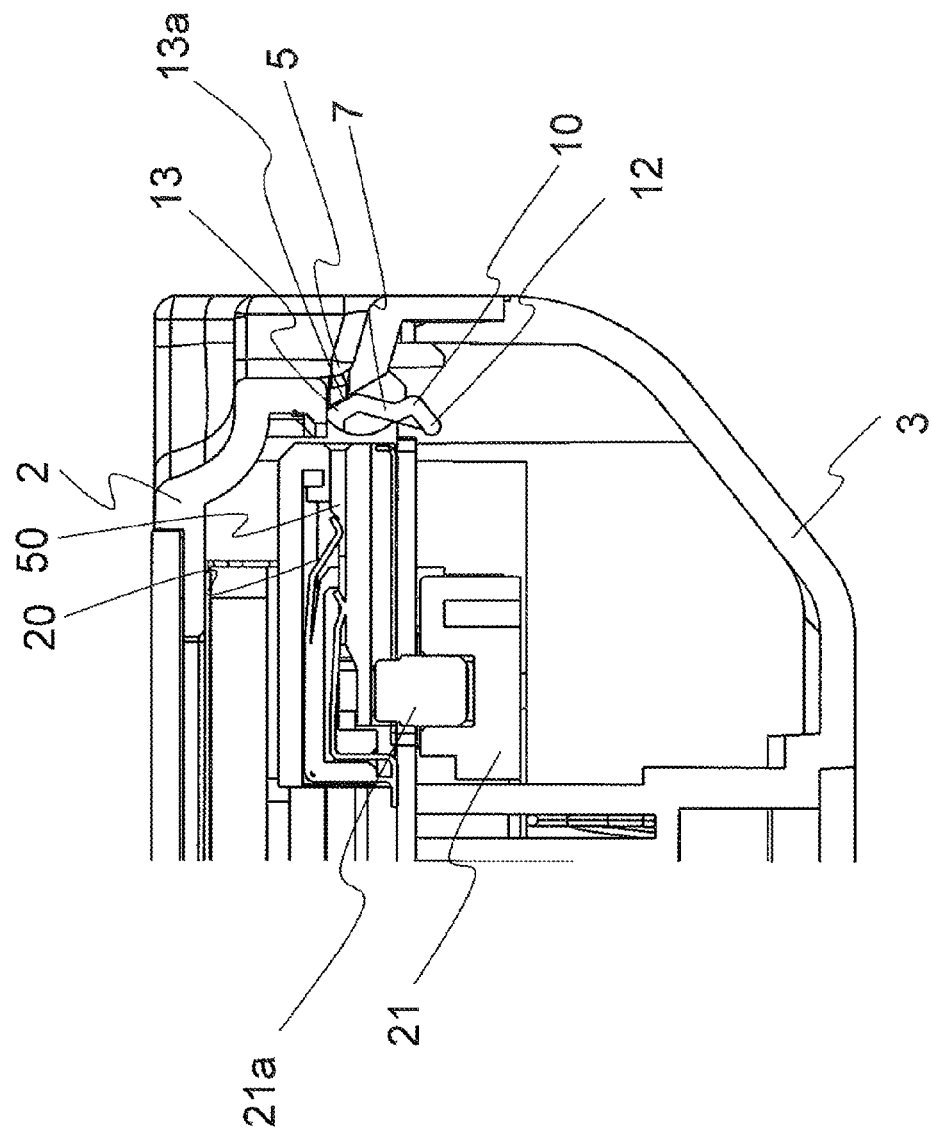
FIG. 7 is a cross section of the main components of the biological sample measurement device in Embodiment 1 of the present invention.

A display component 4 for displaying blood glucose level (an example of biological information), for example, is provided on the upper face side of the upper case 2. A sensor insertion opening 5 that is wider than it is tall is provided on the distal end side of the upper case 2. As shown in FIG. 7, a sensor insertion component 50, which is the space into which a sensor is inserted, is formed behind the sensor insertion opening 5. In Embodiment 1, the upper face side of the upper case 2 is referred to as "above" (the upper side), and the lower face side of the lower case 3 is referred to as "below" (the lower side). We will let the side on which the sensor insertion opening 5 is provided be the front (front side) of the main body case 1, and the opposite side the rear (rear side). The lateral direction shall be a direction that is perpendicular to the direction in which the sensor is inserted, and a direction parallel to the upper face where the display unit 4 is provided.

An ejection manipulation component, which constitutes part of the sensor ejection mechanism, is disposed on the surface of the main body case 1.

Figure 13:
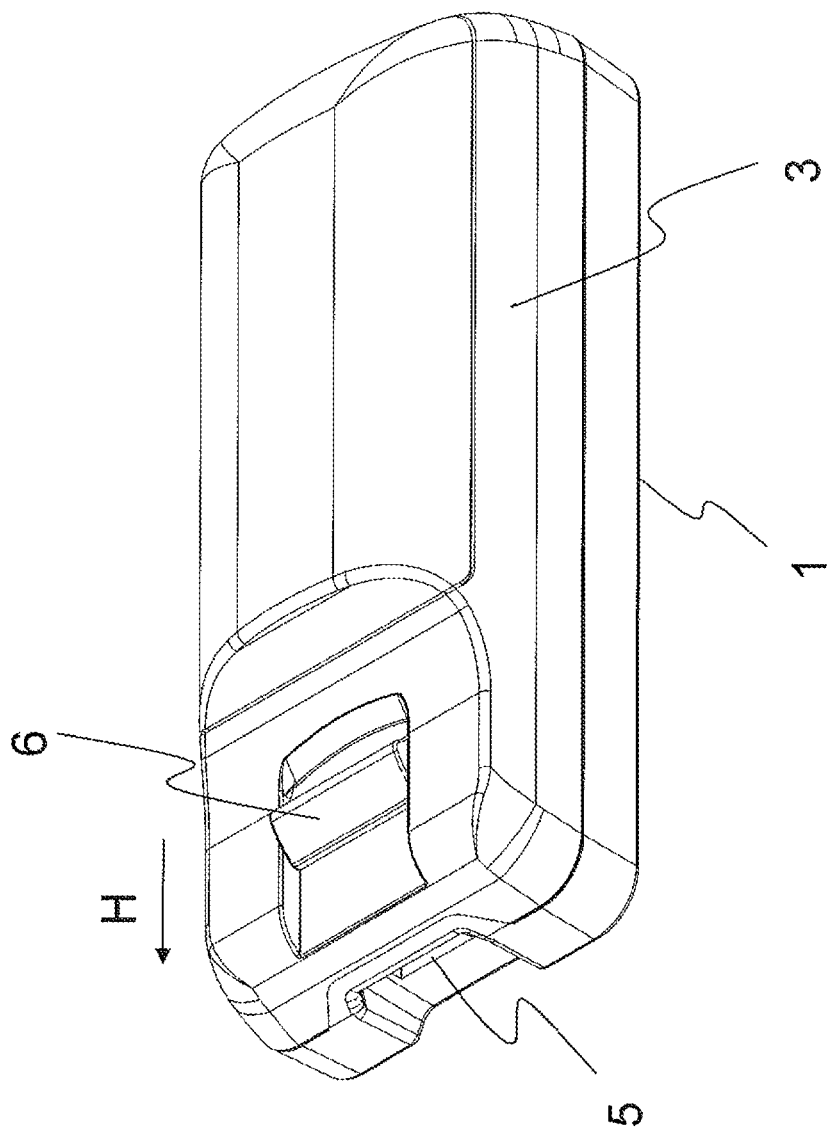
FIG. 13 is a diagram of an example of the layout of an ejection manipulation component of the biological sample measurement device in Embodiment 1 of the present invention.

FIG. 13 shows an ejection manipulation component 6 as an example of the specific configuration of the ejection manipulation component.

Specifically, the ejection manipulation component 6, which is able to slid in the longitudinal direction toward the sensor insertion opening 5, is provided on the lower face side of the lower case 3. This ejection manipulation component 6 may be provided to the upper case 2.

Configuration of Shutter 7

Figure 3:
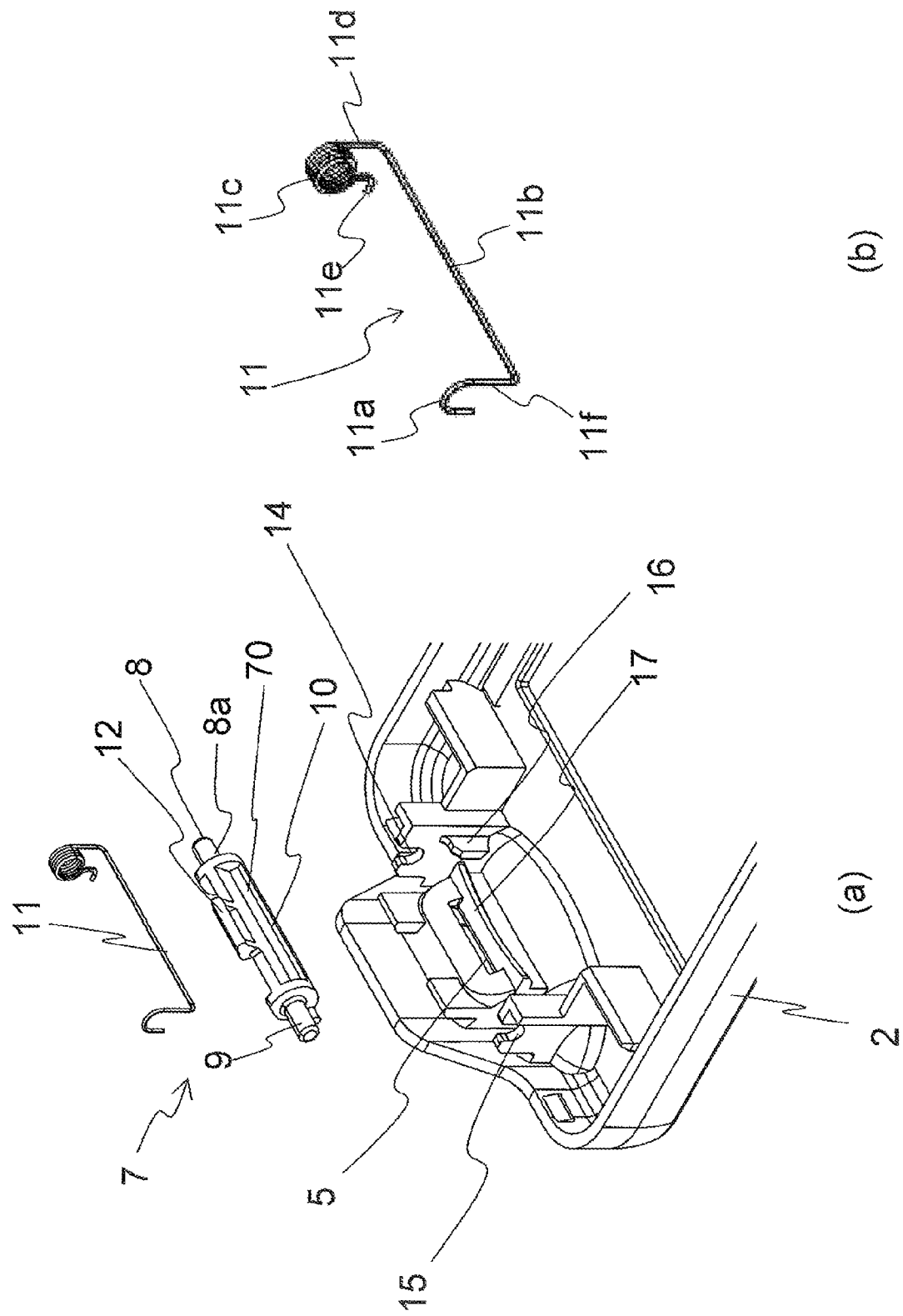
FIG. 3a is an exploded oblique view of the biological sample measurement device in Embodiment 1 of the present invention.
FIG. 3b is an oblique view of a spring in the biological sample measurement device in Embodiment 1 of the present invention.

As shown in FIGS. 2 and 3, in this embodiment a shutter 7 that can be opened and closed is provided behind the sensor insertion opening 5. As shown in FIGS. 3 to 6, this shutter 7 is made up of a rotation component 70 that rotates during insertion and ejection of a sensor 19, and a spring 11 attached to the rotation component 70. The rotation component 70 has shaft components 8 and 9 disposed on both sides of the sensor insertion opening 5, an opening and closing plate 10 that is wider than it is tall and is provided between the shaft components 8 and 9 on both sides, and a manipulated component 12 that is manipulated by the sensor ejection mechanism. As shown in FIG. 7, an opening and closing component 13, which is disposed opposite the sensor insertion opening 5 so as to block off the sensor insertion opening 5 when the sensor insertion opening 5 has been closed, is formed on the opening and closing plate 10. The spring 11 is attached to the shaft components 8 and 9 of the rotation component 70 so as to bias the opening and closing plate 10 in the direction of closing the sensor insertion opening 5.

As shown in FIGS. 6d and 7, an inclined face 13a, which is inclined toward the inside of the sensor insertion opening 5, is formed on the opening and closing component 13 of the opening and closing plate 10. This inclined face 13a is inclined so as to approach the upper face of the upper case 2 as it moves inward in a state in which the sensor insertion opening 5 has been closed.

As shown in FIGS. 6d and 7, the manipulated component 12 is provided on the opposite side from the opening and closing component 13 of the opening and closing plate 10, with a line linking the shaft components 8 and 9 (the axis of the rotation component 70) in between.

That is, as shown in FIG. 7, in this embodiment the shutter 7 is provided openably and closeably on the inside of the sensor insertion opening 5, and the opening and closing component 13 is biased by the spring 11 in the direction of closing the sensor insertion opening 5.

The shutter 7 portion will now be described in further detail.

Figure 4:
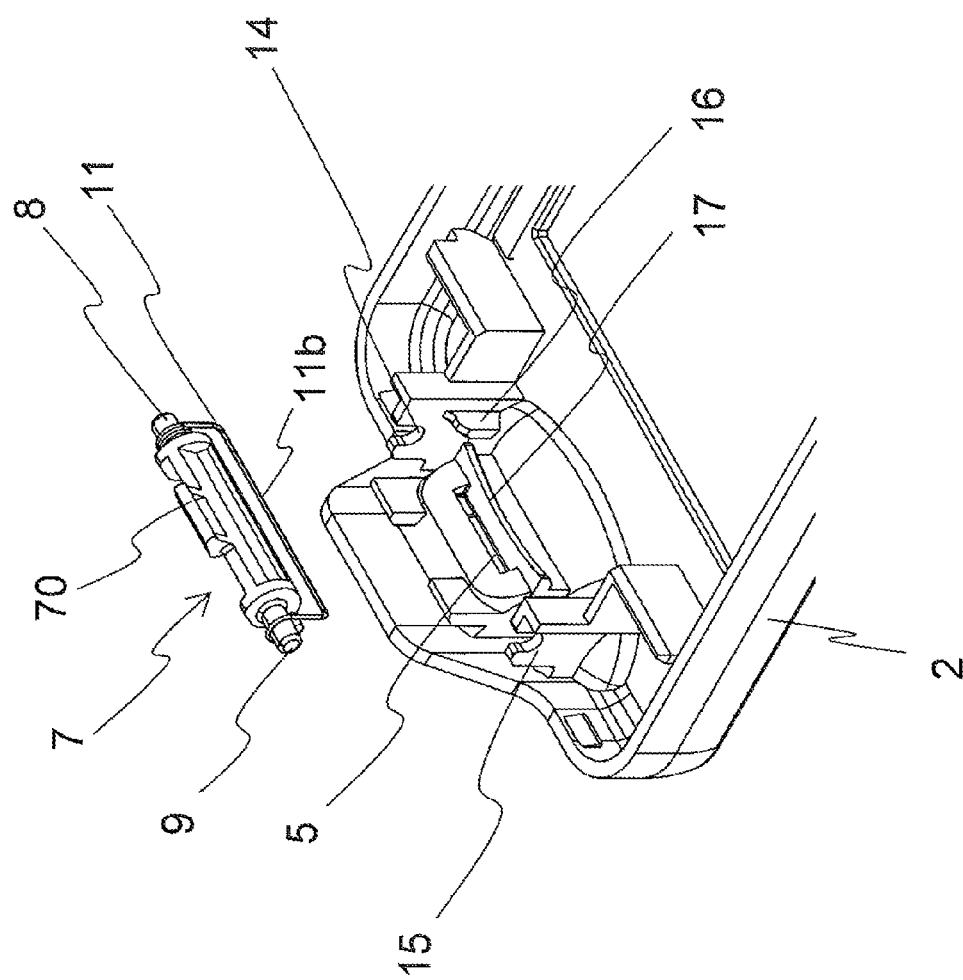
FIG. 4 is an exploded oblique view of the biological sample measurement device in Embodiment 1 of the present invention.
Figure 5:
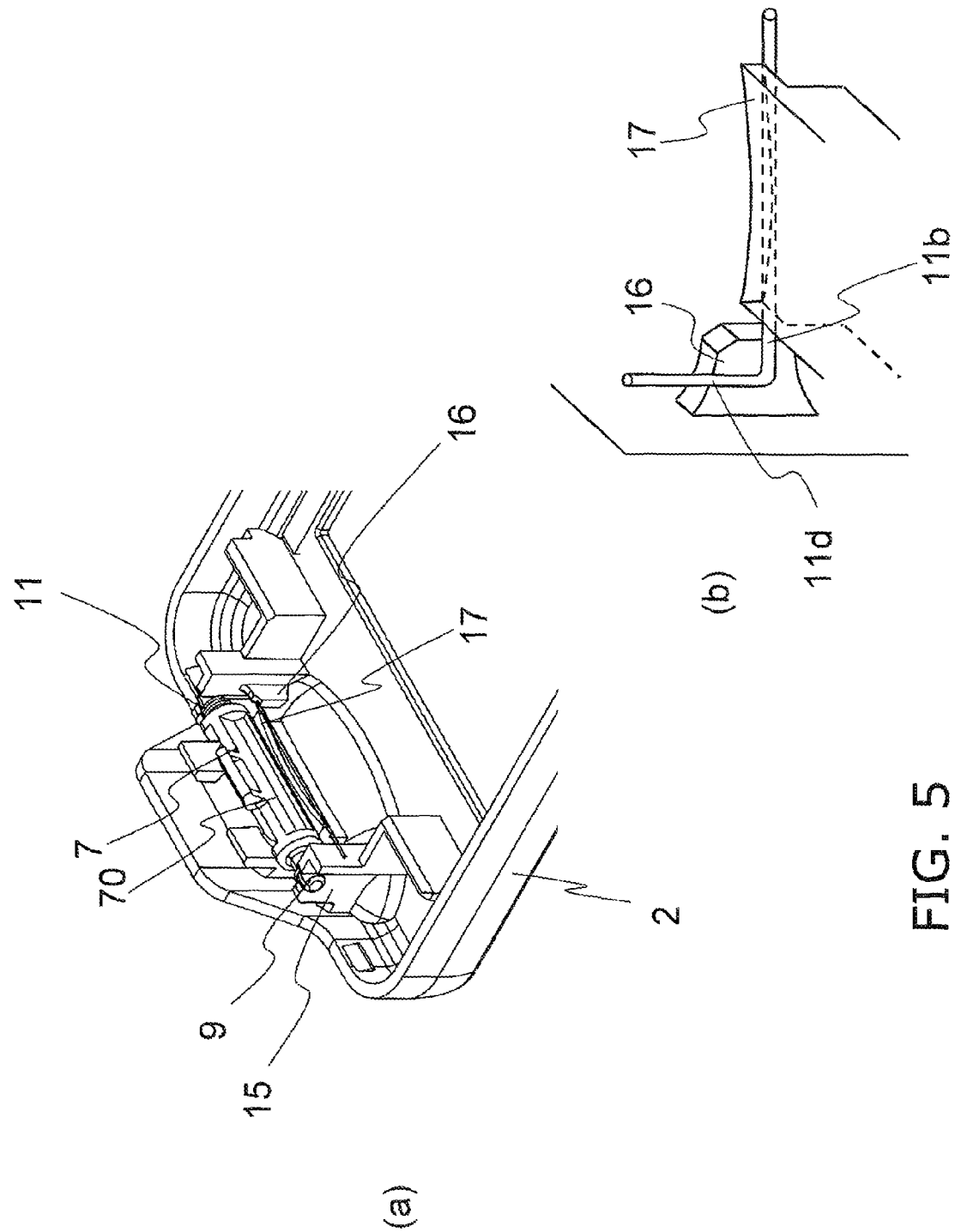
FIG. 5a is an exploded oblique view of the biological sample measurement device in Embodiment 1 of the present invention.
FIG. 5b is a detail see-through oblique view of the biological sample measurement device in Embodiment 1 of the present invention as seen from the front.
Figure 6:
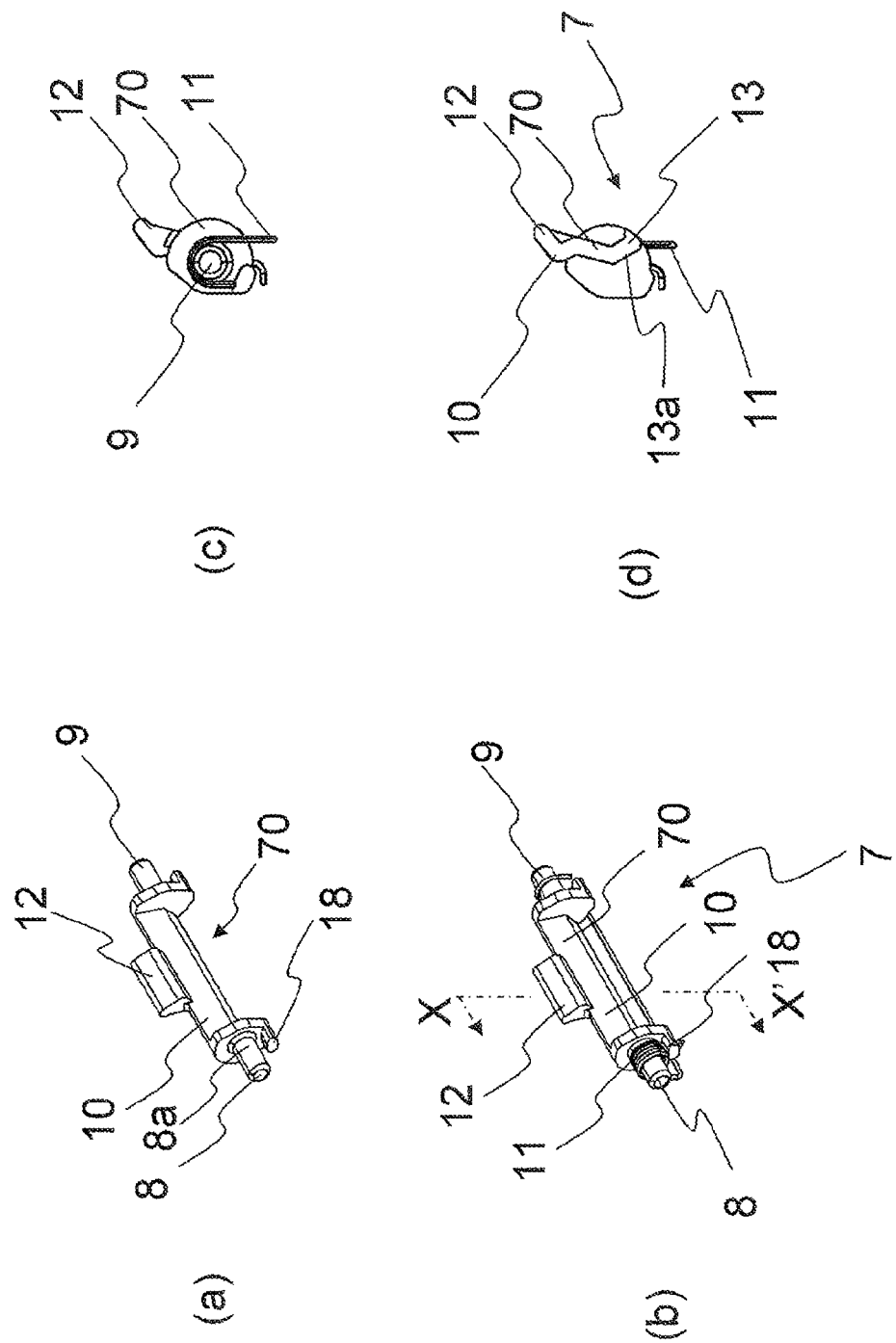
FIG. 6a is an oblique view of a rotation component of a shutter in the biological sample measurement device in Embodiment 1 of the present invention.
FIG. 6b is an oblique view of the shutter.
FIG. 6c is a side view of the shutter.
FIG. 6d is a cross section along the X-X' line in FIG. 6b.

First, as shown in FIGS. 3 to 5a, a shaft component 14 on which the shaft component 8 of the shutter 7 is mounted, and a shaft component 15 on which the shaft component 9 is mounted are provided on both sides of the inside of the sensor insertion opening 5 of the upper case 2. Before the shaft components 8 and 9 of the shutter 7 are supported o these shaft components 14 and 15, the spring 11 is mounted to the shaft components 8 and 9, as shown in FIGS. 4 and 6.

Configuration of Spring 11

As shown in FIG. 3b, this spring 11 has an engagement component 11a which is curved so as to engage with the shaft component 9 and which is formed at one end thereof, a straight portion 11b which is formed on the upper case 2 side along the lateral direction of the rotation component 70, and a coil spring component 11c that is formed in a coil spring shape at the other end, that is, on the opposite side from the engagement component 11a with the straight portion 11b in between. The spring 11 is mounted to the rotation component 70 in a state in which the engagement component 11a is engaged with the shaft component 9 and the shaft component 8 has been passed through the center part of the coil spring component 11c. More precisely, a straight portion 11f, which is formed vertically toward the opposite side of the upper case 2 (downward) from the straight portion 11b, is formed between the straight portion 11b and the engagement component 11a, and a straight portion 11d, which is formed toward the opposite side of the upper case 2 (downward) from the straight portion 11b, is formed between the straight portion 11b and the coil spring component 11c. Also, an engaged component 11e that is engaged with an engagement component 18 is formed at the distal end on the side of the spring 11 where the coil spring component 11c is formed.

Specifically, as shown in FIG. 3, the spring 11 is engaged at one end with the shaft component 9, and the other end out of the straight portion on the upper case 2 side of the opening and closing plate 10 is formed in a coil spring shape, and is mounted to the rotation component 70 in a state in which the shaft component 8 has been passed through the center part thereof.

Mounting of Shutter 7

In the above configuration, when the shutter 7 is mounted to the shaft components 14 and 15, first the spring 11 is mounted to the rotation component 70 as shown in FIG. 4. Then, in supporting the shaft component 8 on the shaft component 14, as shown in FIG. 5b, the other end (the shaft component 8 side) of the straight portion 11b of the spring 11 is passed between protrusions 16 and 17 provided on the upper case 2 side of the shaft component 14, and is hooked on the upper case 2 side of the protrusion 17, and then the shaft component 8 is supported on the shaft component 14. Here, the shaft component 14 supports the shaft component 8 on the outside of the portion of the shaft component 8 where the coil spring component 11c is mounted. This portion of the shaft component 8 where the coil spring component 11c is mounted is shown by 8a in FIG. 3, and corresponds to an example of a coil spring mounting component.

FIG. 5b is a see-through diagram of FIG. 5a as seen from the front, and is a simplified diagram in which the rotation component 70 has been omitted in order to illustrate the state of the spring 11 and the protrusions 16 and 17.

The protrusions 16 and 17 will now be described.

First, the protrusion 16 is provided in the vertical direction of the upper case 2 and the lower case 3 (the thickness direction of the main body case 1), and as shown in FIG. 5b, the straight portion 11b and the straight portion 11d of the spring 11 come into contact, which biases the shutter 7 in the direction of closing the sensor insertion opening 5. As shown in FIG. 6b, to bias the shutter 7 in this way, the other end of the spring 11, that is, the engaged component 11e, is engaged with the engagement component 18.

As shown in FIGS. 3 and 5b, the protrusion 17 is formed protruding inward in the lateral direction of the sensor insertion opening 5 and above the sensor insertion opening 5, and prevents the spring 11 from coming loose on the opposite side from the upper case 2 (downward) by interfering with the straight portion 11b of the spring 11.

Finally, the shaft component 9 of the shutter 7 is supported on the shaft component 15, and as shown in FIG. 5a, the shutter 7 is mounted openably and closeably behind the sensor insertion opening 5. A cross section of this state is shown in FIG. 7. As shown in FIG. 7, an inclination is provided to the opening on the inside of the main body case 1 where the sensor insertion opening 5 is formed so that the upper case 2 side will be to the rear and the lower case 3 side at the front.

Figure 14:
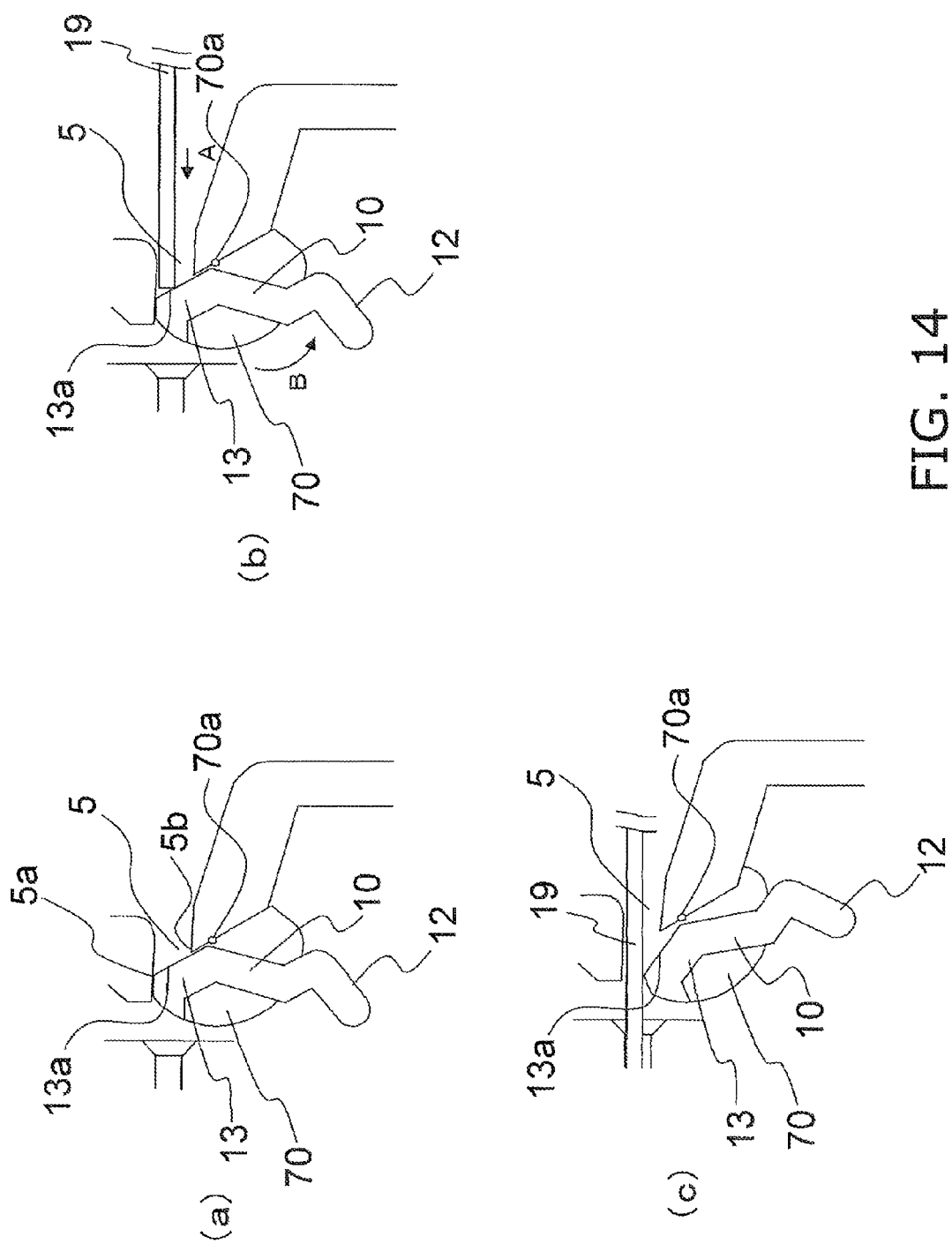
FIGS. 14a to 14c are detail cross sections schematically illustrating the state near the sensor insertion opening when a sensor has been inserted into the biological sample measurement device in Embodiment 1 of the present invention.

Specifically, the inclination of the sensor insertion opening 5 means that the position of the upper edge 5a forming the sensor insertion opening 5 is farther to the inside than the location of the lower edge 5b. The simplified diagram in FIG. 14a shows the upper edge 5a and the lower edge 5b of the sensor insertion opening 5.

Figure 8:
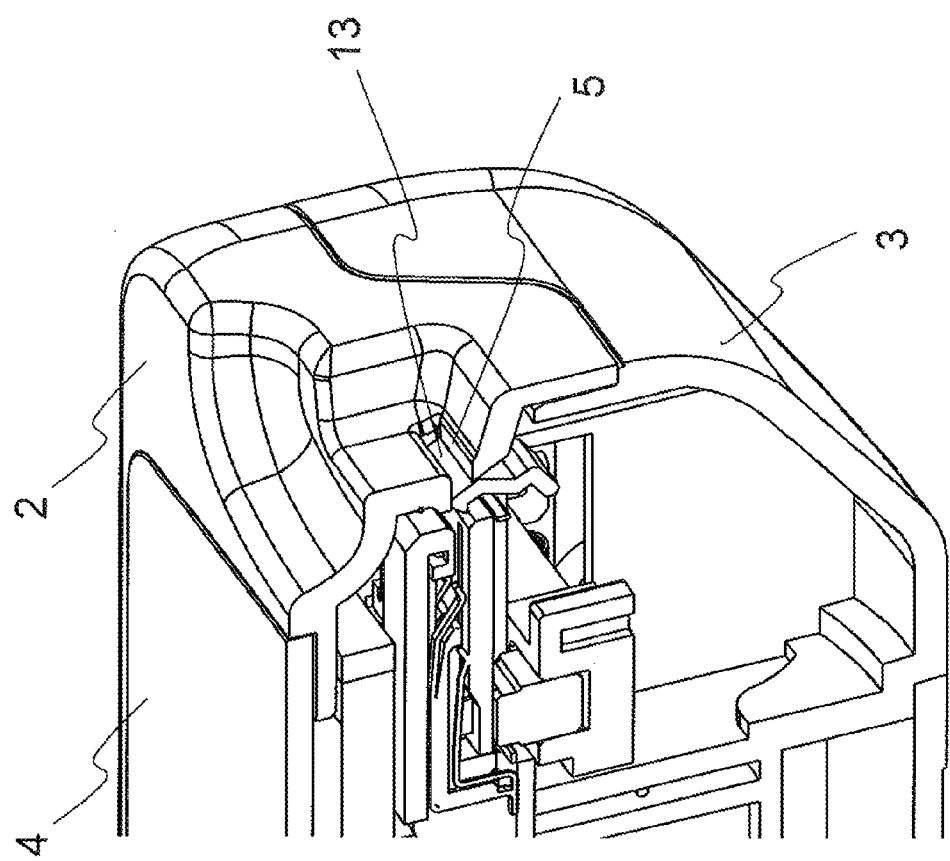
FIG. 8 is an oblique view in which part of the main components of the biological sample measurement device in Embodiment 1 of the present invention has been cut away.

The opening and closing component 13 of the shutter 7 openably and closeably covers the sensor insertion opening 5 thus inclined, as shown in FIGS. 7 and 8.

Therefore, as shown in FIG. 7, the opening and closing component 13 also has a shape provided with the inclined face 13a in which the upper case 2 side is to the rear and the lower case 3 side is at the front. That is, the sensor insertion opening 5 is closed by the opening and closing component 13 of the shutter 7, so the configuration of the biological sample measurement device in this embodiment affords a reduction in unwanted intrusion of dust or liquid through the sensor insertion opening 5.

Operation of Biological Sample Measurement Device

Figure 9:
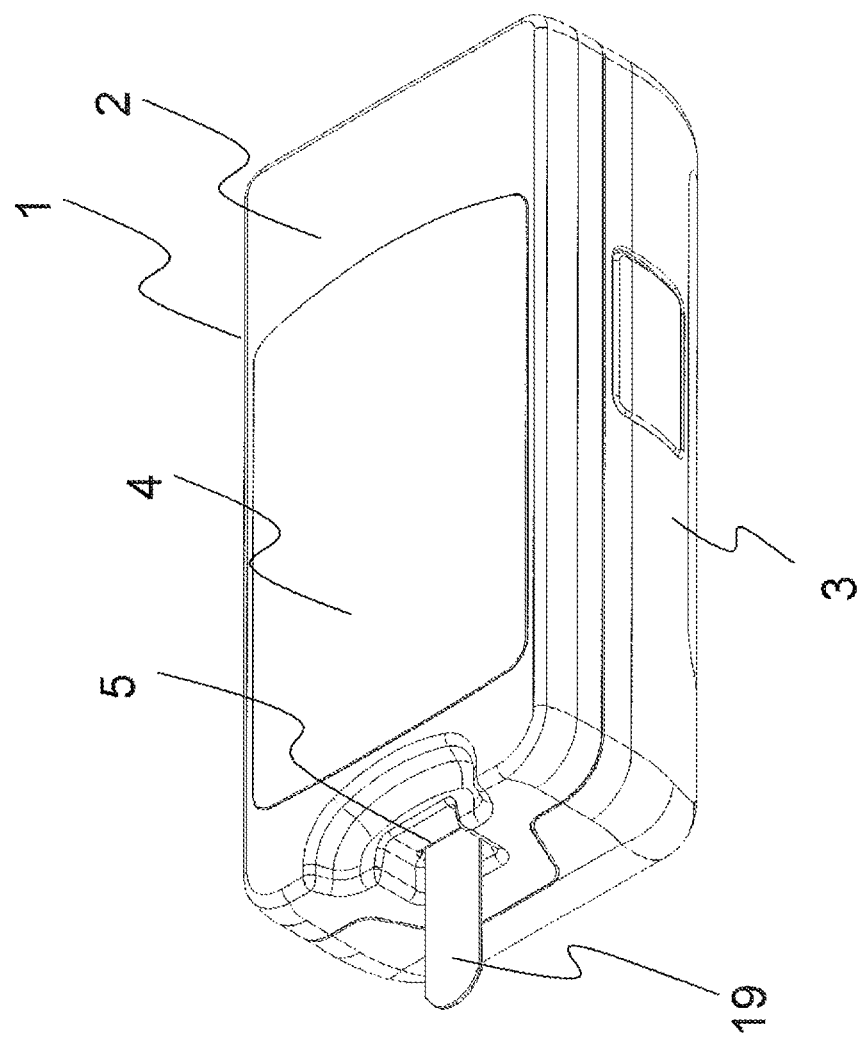
FIG. 9 is an oblique view of a state in which a sensor has been inserted into the biological sample measurement device in Embodiment 1 of the present invention.
Figure 11:
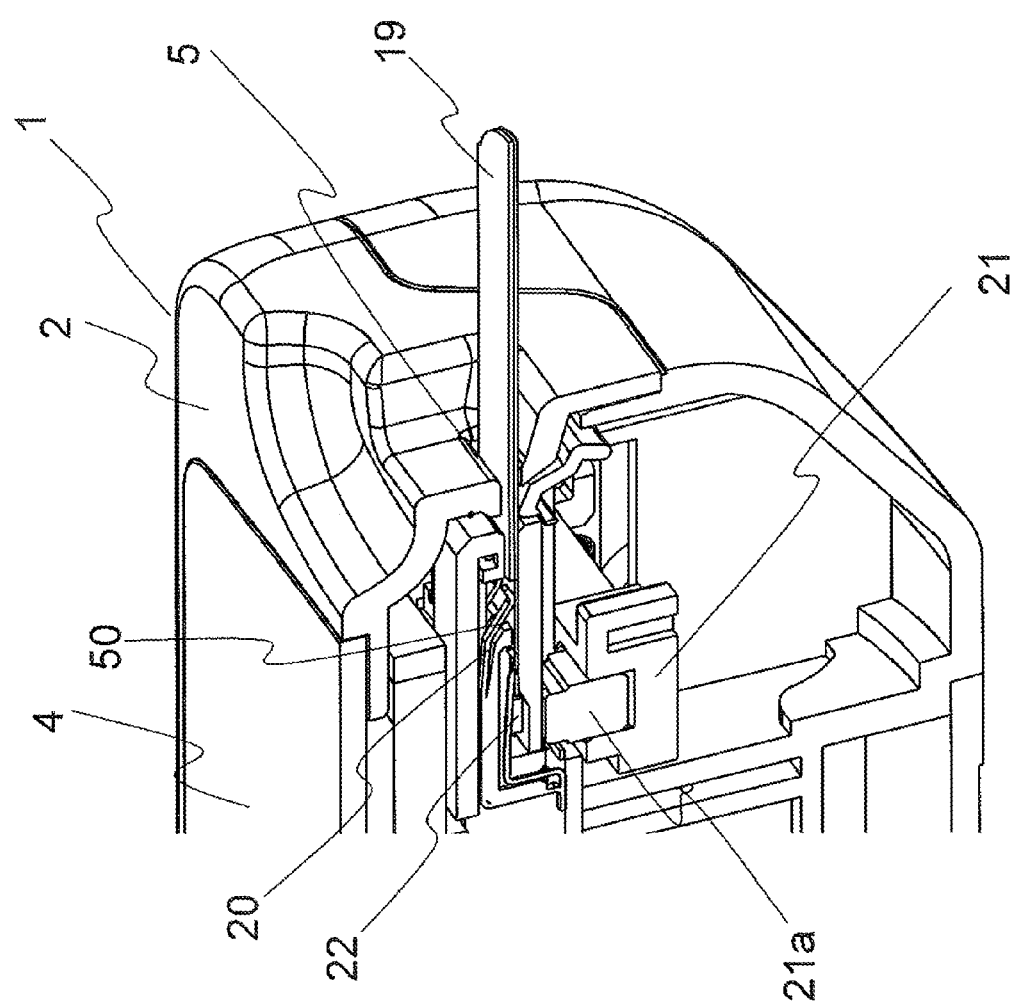
FIG. 11 is an oblique view in which part of the biological sample measurement device in Embodiment 1 of the present invention has been cut away.

FIGS. 9 and 11 show a state in which the blood glucose level, for example, is measured by inserting the sensor 19 through the sensor insertion opening 5 in this configuration.

Operation During Sensor Insertion

First, when a side of an electrode component provided to the rear end of the sensor 19 is pushed into the main body case 1 through the sensor insertion opening 5, the opening and closing component 13 of the shutter 7 that was covering the sensor insertion opening 5 is pushed open by the sensor 19 in the inclination direction of the opening and closing component 13. More precisely, as shown in FIGS. 14*a* and 14*b*, when the sensor 19 is inserted into the sensor insertion opening 5 (see the arrow A), the rear end of the sensor 19 hits the inclined face 13*a* of the opening and closing component 13. Then, when the sensor 19 is pushed in along the inclination of the inclined face 13*a*, as shown in FIG. 14*c*, the opening and closing component 13 rotates (see the arrow B) and the sensor insertion opening 5 opens. The rotational axis of the rotation component 70 having the opening and closing component 13 is indicated by 70*a* in FIGS. 14*a* to 14*c*.

As a result, the electrode component of the sensor 19 is electrically connected to a connection terminal 20 provided behind the sensor insertion opening 5 inside the main body case 1. The connection terminal 20 is an elastic member, and the connection terminal 20 is electrically connected to the electrode component of the sensor 19 by this elastic force.

In this state, if blood is deposited onto a deposition component (not shown) provided on the distal end side of the sensor 19, the blood glucose level is measured and this value is displayed on the display component 4.

Operation During Sensor Ejection

Figure 10:
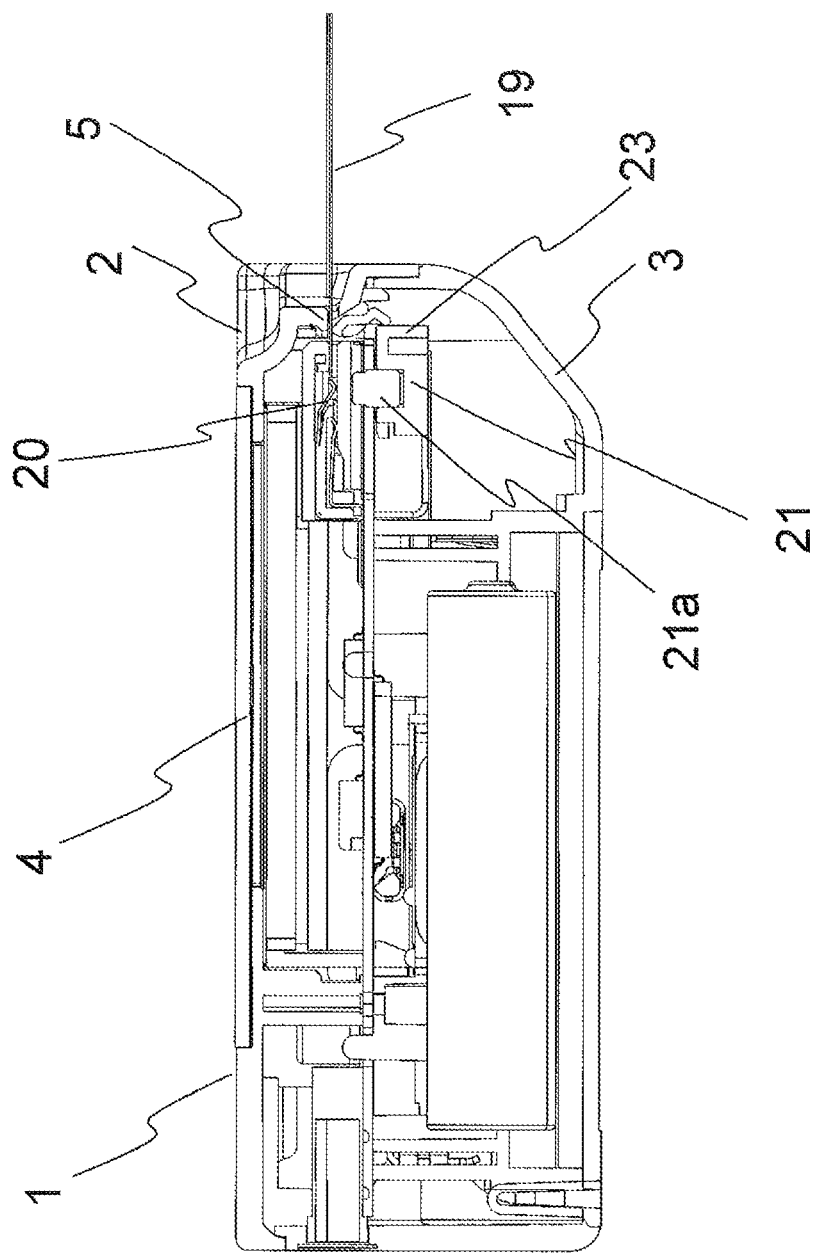
FIG. 10 is a cross section of the biological sample measurement device in Embodiment 1 of the present invention.
Figure 12:
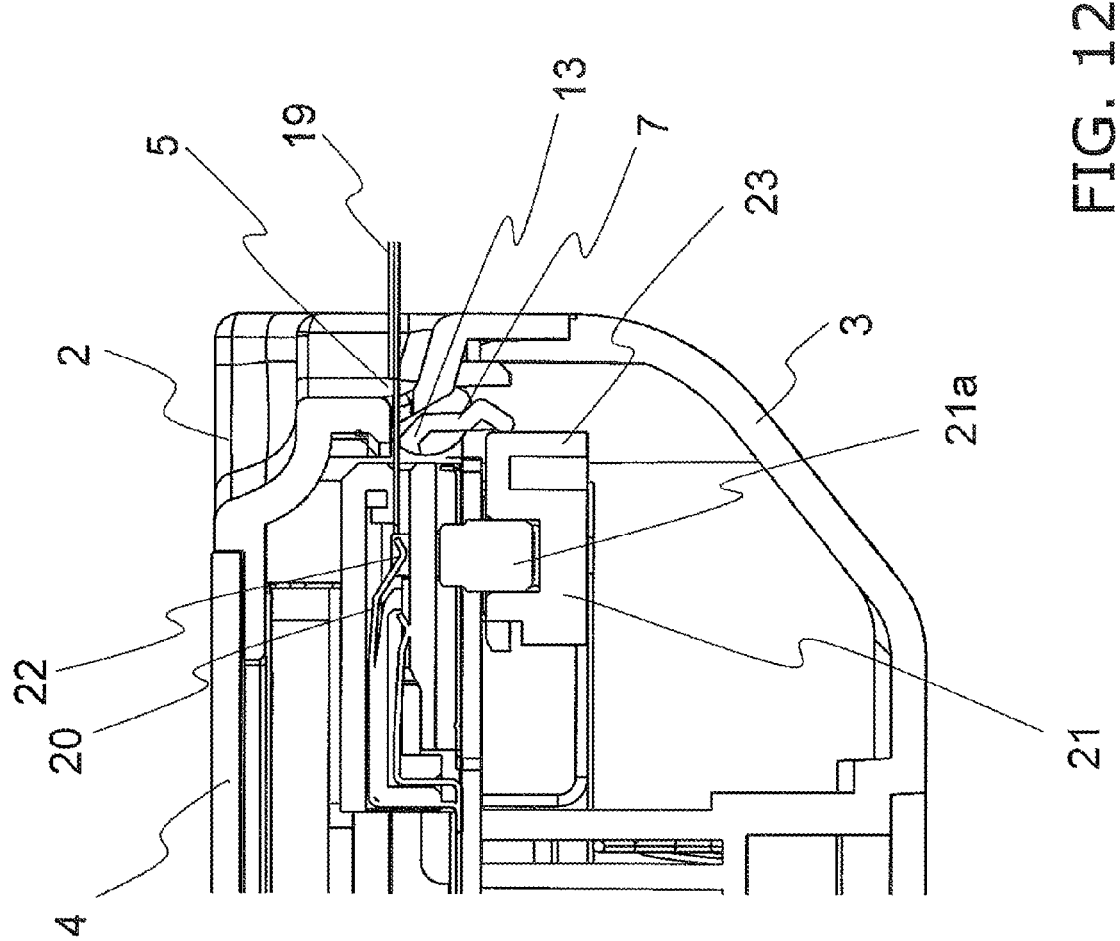
FIG. 12 is a cross section of the main components of the biological sample measurement device in Embodiment 1 of the present invention.

When this measurement of the blood glucose level is finished, the sensor 19 is ejected. This ejection of the sensor 19 is accomplished by pushing the ejection manipulation component 6 shown in FIG. 13 forward (the sensor insertion opening 5 side; see the arrow H). The ejection manipulation component 6 is connected to a lever 21 by a linking component (not shown; see FIG. 11). Therefore, when the ejection manipulation component 6 is pushed forward, the levers 21 and 21*a* that move in conjunction with it inside the main body case 1 move forward as shown in FIGS. 10, 11 and 12, and this operation of the levers 21 and 21*a* results in the ejection of the sensor 19. Furthermore, as show in FIGS. 10 to 12, the lever 21 is formed so as to sandwich the lever 21*a*, and when the lever 21 is moved forward, the lever 21*a* also moves forward at the same time.

Figure 17:
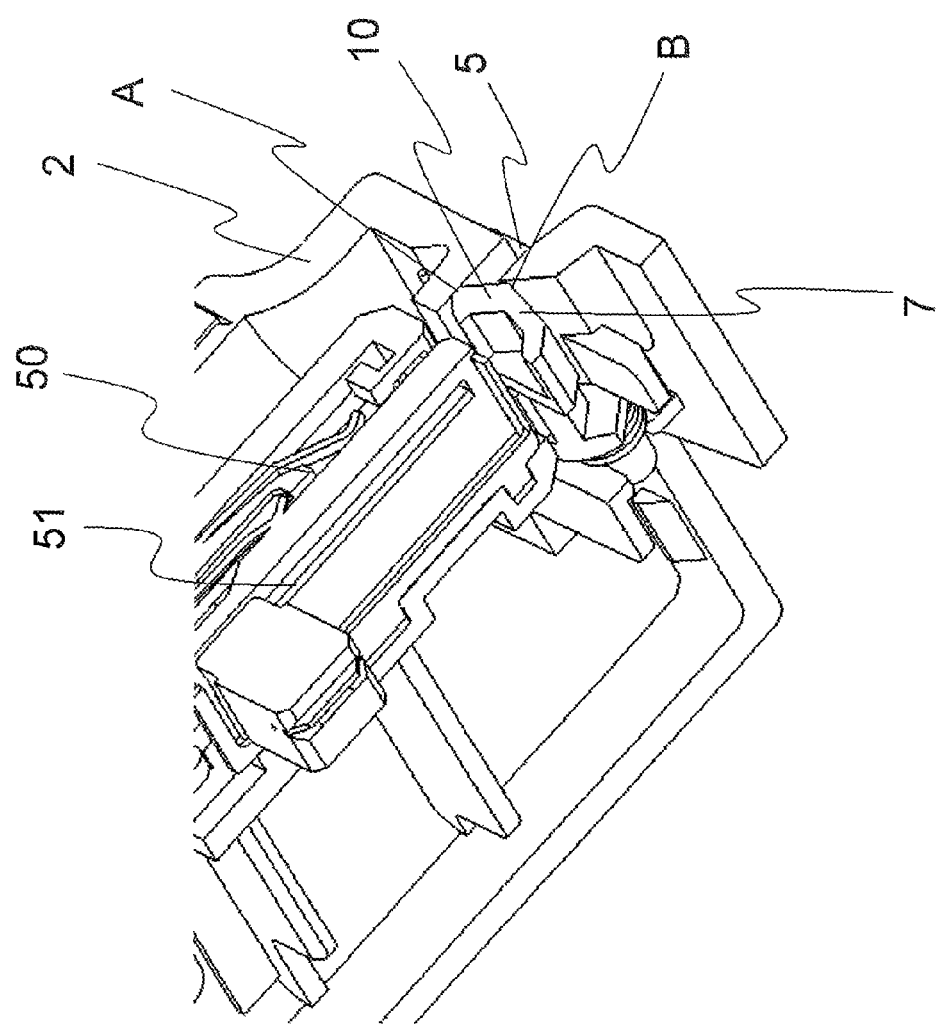
FIG. 17 is a detail oblique view of the main components of the biological sample measurement device in Embodiment 1 of the present invention.
Figure 18:
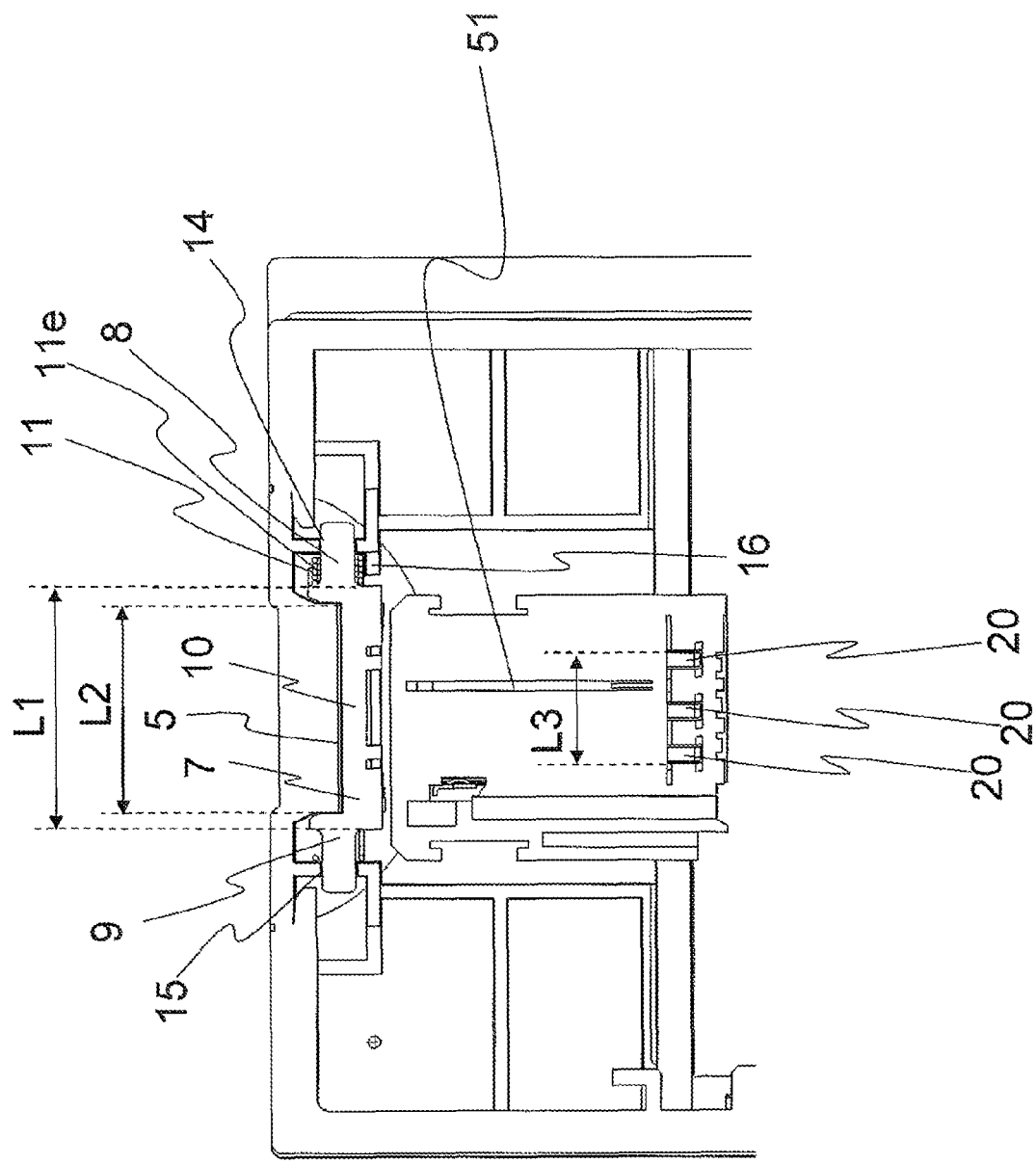
FIG. 18 is a detail plan view of the main components of the biological sample measurement device in Embodiment 1 of the present invention.

More specifically, the manipulation component 22 of the lever 21*a* hits the rear end side of the sensor 19, so when the manipulation component 22 of the lever 21*a* is moved forward by the ejection manipulation component 6, the sensor 19 moves through the sensor insertion opening 5 and out of the main body case 1, as shown in FIGS. 10 and 12. Also, as shown in FIGS. 17 and 18, a slit 51 is formed in the longitudinal direction on the lower face of the sensor insertion component 50, which is the space into which the sensor 19 is inserted. The manipulation component 22 (see FIG. 11) is provided to the lever 21*a* so as to protrude from the lever 21*a*, through the slit 51, and into the sensor insertion component 50.

In this embodiment, before the sensor 19 is ejected out of the main body case 1 from this state in FIGS. 10 and 12, the shutter 7 is opened up. That is, when the sensor 19 has been moved forward (see FIGS. 10 and 12) from a state in which the sensor 19 was inserted through the sensor insertion opening 5 into the main body case 1 (see FIG. 11), the result is a state in which the opening and closing component 13 of the shutter 7 is in contact with the lower face side of the sensor 19.

Furthermore, as shown in FIGS. 10, 12, and 14*c*, the upper side of the opening and closing component 13 at this point hits the sensor 19, resulting in an inclined state in which the lower side is located farther forward than the upper side. Accordingly, before the sensor 19 is ejected through the sensor insertion opening 5 out of the main body case 1 by moving the manipulation component 22 of the lever 21*a* forward, the opening and closing component 13 needs to be moved away from the sensor 19 to open up the opening and closing component 13 of the shutter 7. That is, unless the shutter 7 is opened up, there is the risk that the ejection of the sensor 19 will be hampered, so an operation in which the shutter 7 is opened up is performed during this ejection.

In view of this, in this embodiment a manipulation component 23 is provided on the sensor insertion opening 5 side of the lever 21. As shown in FIG. 12, when this manipulation component 23 pushes the manipulated component 12 of the shutter 7 forward, the opening and closing component 13 of the shutter 7 rotates counter-clockwise, and this opens up the shutter 7.

Therefore, the sensor 19 can be easily ejected through the sensor insertion opening 5 and out of the main body case 1 by pushing the rear end of the sensor 19 forward with the manipulation component 22 of the lever 21*a*.

Figure 15:
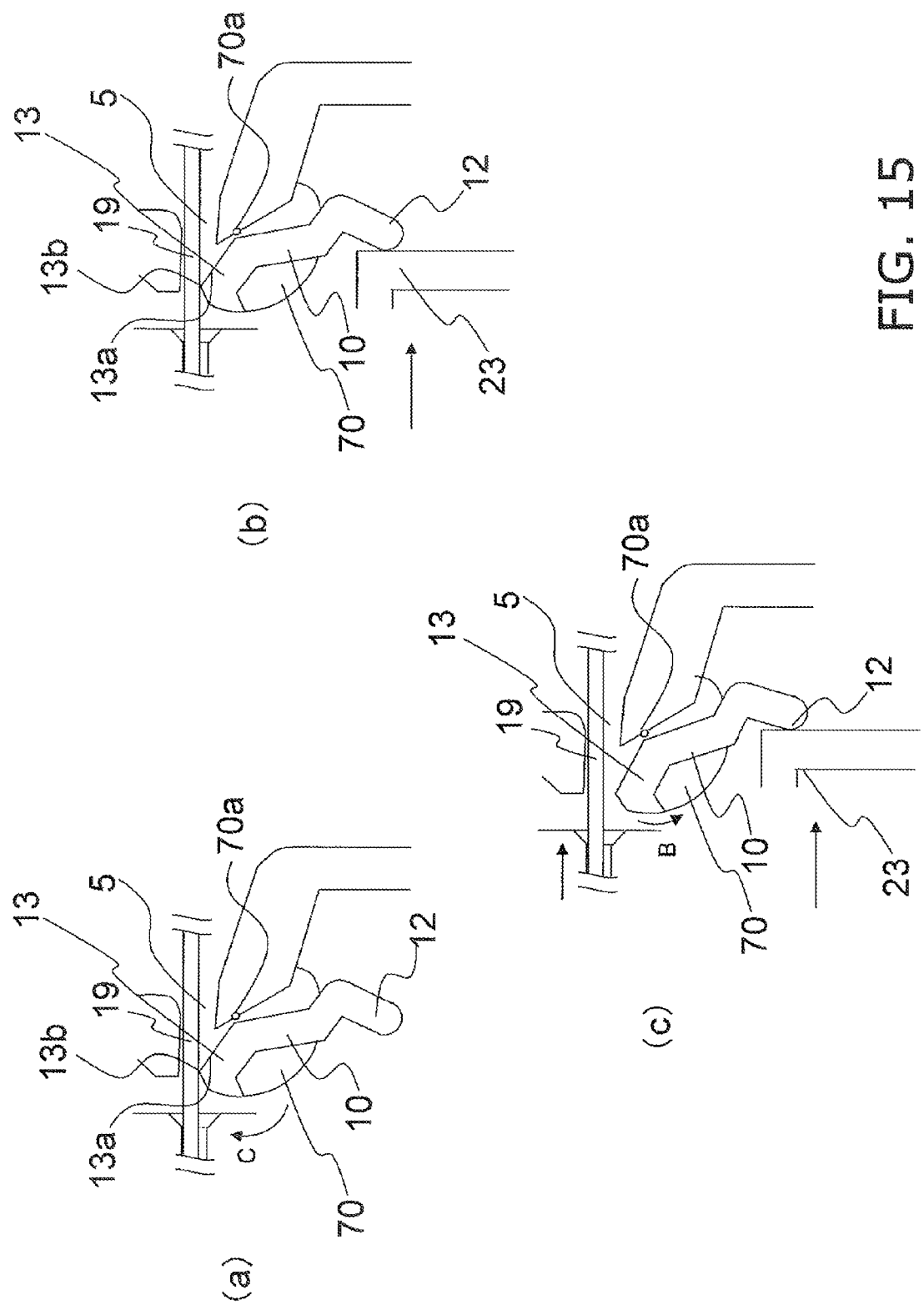
FIGS. 15a to 15c are detail cross sections schematically illustrating the state near the sensor insertion opening when a sensor has been ejected from the biological sample measurement device in Embodiment 1 of the present invention.

To describe this in greater detail, as shown in FIG. 15*a*, since the rotation component 70 is biased by the spring 11 (see FIG. 4) in the direction of closing the sensor insertion opening 5 (the direction of the arrow C), the sensor 19 is pushed downward by the opening and closing component 13. This keeps the sensor 19 from falling out of the sensor insertion opening 5. In FIG. 15*a*, the portion of the opening and closing component 13 that is in contact with the sensor 19 is indicated as the contact component 13*b*. Meanwhile, when the ejection manipulation component 6 is moved forward in the ejection of the sensor 19, the sensor 19 is moved forward by the manipulation component 23 of the lever 21*a*. As the sensor 19 is thus moved forward, as shown in FIG. 15*b*, the manipulation component 23 hits the manipulated component 12 of the shutter 7. When the ejection manipulation component 6 is moved farther forward, as shown in FIG. 15*c*, the manipulated component 12 of the rotation component 70 is pushed forward by the manipulation component 23 of the lever 21, so the rotation component 70 rotates in the direction of the arrow B, and the pushing of the sensor 19 by the opening and closing component 13 is released. The sensor 19 can be ejected by further moving the ejection manipulation component 6 forward.

The timing at which the pushing of the sensor 19 is released is preferably after the sensor 19 has moved away from the connection terminal 20. This is because the sensor 19 may shoot away from the main body case 1 under the elastic force of the connection terminal 20 when the sensor 19 is moving away from the connection terminal 20, but if the sensor 19 is pressed on by the opening and closing component 13, this shooting out of the sensor will be less likely to occur.

Other Features

Other features of this embodiment will now be described.

In this embodiment, as discussed above in reference to FIGS. 7 and 8, the sensor insertion opening 5 is openably and closeably covered by the opening and closing component 13 of the shutter 7. That is, the sensor insertion opening 5 has been closed by the opening and closing component 13 of the shutter 7, so the biological sample measurement device in this embodiment is configured such that there is a reduction in unwanted intrusion of dust or liquid through the sensor insertion opening 5.

Figure 16:
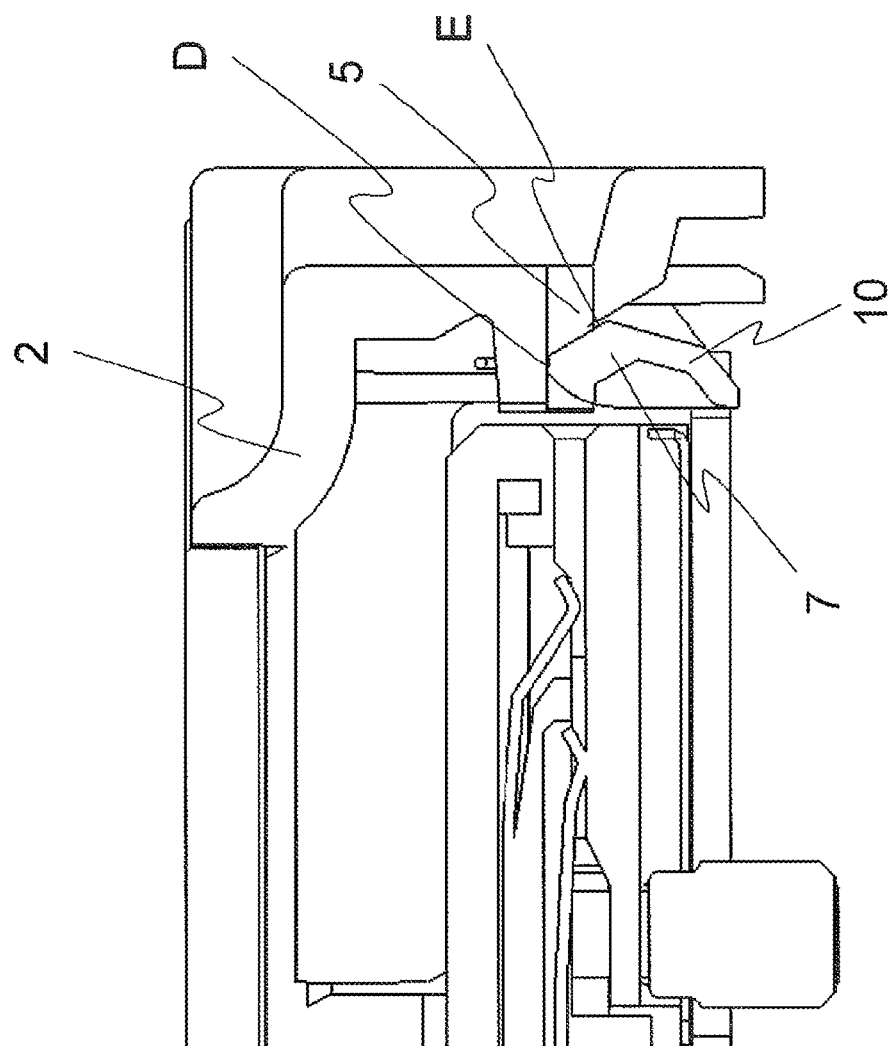
FIG. 16 is a detail cross section of the main components of the biological sample measurement device in Embodiment 1 of the present invention.

In a state in which the sensor insertion opening 5 has been closed by the shutter 7, as shown in FIGS. 16 and 17, closing components D and E are formed when the upper case 2 and the opening and closing plate 10 of the shutter 7 come into contact or close proximity to the inside of the sensor insertion opening 5.

As shown in FIG. 18, these closing components D and E are formed in the lengthwise direction of the opening and closing plate 10. The opening and closing plate 10, which is wider than it is tall, is formed so that it is larger in the lateral direction than the sensor insertion opening 5, which is also wider than it is tall. In FIG. 18, the length of the opening and closing plate 10 in the lateral direction is indicated by L1, and the length of the sensor insertion opening 5 in the lateral direction is indicated by L2.

As shown in FIG. 18, the length L1 of the opening and closing plate 10 in the lateral direction is greater than the dimension of the connection terminal 20 in the lateral direction.

In this embodiment, as shown in FIG. 18, the connection terminal 20 is configured such that three of the connection terminals 20 are disposed side by side in the lateral direction of the sensor insertion opening 5, so the dimension of the connection terminal 20 in the lateral direction indicates the dimension between the left and right connection terminals 20. This dimension of the connection terminal 20 in the lateral direction is indicated as L3 in FIG. 18.

That is, the length L1 in the lateral direction of the opening and closing plate 10 of the shutter 7 is greater than the length L2 in the lateral direction of the sensor insertion opening 5, which suppresses the inflow of liquid through the sensor insertion opening 5.

Also, even though the inflow of liquid through the sensor insertion opening 5 is thus suppressed by the shutter 7, since the opening and closing plate 10 of the shutter 7 has the closing components D and E that are formed in contact with or close proximity to the upper case 2 to the inside of the sensor insertion opening 5, there may be situations in which some of the liquid that has flowed in through the sensor insertion opening 5 adheres to the capillary portion formed here.

Liquid adhering to the closing components D and E spreads out by capillary action on both sides in the lateral direction of the opening and closing plate 10. As discussed above in reference to FIG. 18, the opening and closing plate 10 is formed so that the length L1 in the lateral direction is greater than the length L3 in the lateral direction of the connection terminal 20, so any liquid that adheres to the closing components D and E and spreads out on both sides in the lateral direction of the opening and closing plate 10 will be guided to the outside of the connection terminal 20.

That is, liquid adhering to the closing components D and E will be less likely to form drops that fall onto the connection terminal 20 portion. As a result, soiling of the connection terminal 20 can be reduced as much as possible, and a decrease in reliability of measurement accuracy can be suppressed.

Also, in this embodiment a decrease in reliability of measurement accuracy can also be suppressed from the following standpoints.

Figure 19:
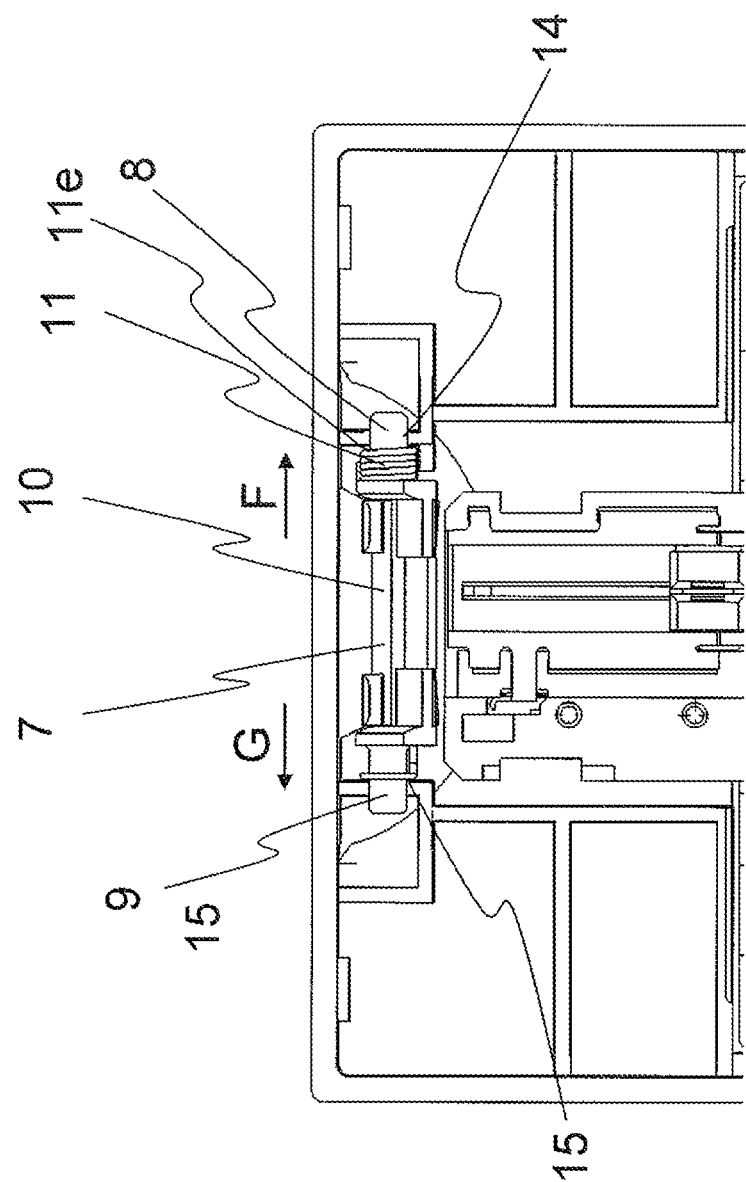
FIG. 19 is a detail plan view of the main components of the biological sample measurement device in Embodiment 1 of the present invention.

Specifically, some of the liquid that flows in through the sensor insertion opening 5 will spread outward through the closing components D and E of the opening and closing plate 10 as discussed above (see the directions of the arrows F and G in FIG. 19), but this liquid that has spread outward can then be made to flow further outside along the spring 11 as shown in FIGS. 18 and 19. To describe this in more specific terms, the coil spring component 11*c* is formed on the spring 11, and this coil spring component 11*c* is mounted around the outer periphery of the shaft component 8 of the shutter 7.

That is, liquid that has spread outward along the closing components D and E then further spreads outward along the capillaries formed between the coil spring coils. The outer portion of the shaft component 8 where the spring 11 is mounted is supported by the shaft component 14, and this configuration forms a capillary between the shaft component 14 and the shaft component 8.

The liquid moves further outward along the capillary of the portion between the shaft component 14 and the shaft component 8. As a result, this helps prevent liquid adhering to the closing components D and E from forming drops that fall onto the connection terminal 20 and soil the connection terminal 20. Consequently, a decrease in reliability of measurement accuracy is also suppressed.

In this embodiment, the opening and closing plate 10 and the shaft components 8 and 9 are formed from a synthetic resin, but the spring 11 having the coil spring component 11*c* is formed from metal.

The surface of the spring 11 having this coil spring component 11*c* is configured so that the metal surface is exposed.

That is, for the capillary action of the spring 11 portion having the coil spring component 11*c* to be strongly manifested, in this embodiment the spring 11 is formed from a metal with better wettability than a resin, and this metal surface is exposed. This configuration results in better capillary action at the spring 11 portion.

Action and Effect

As discussed above, a biological sample measurement device that is convenient to use can be provided because the job of inserting the sensor 19 is made easier.

Specifically, since the openable and closeable shutter 7 is provided inside the main body case 1, it is less likely that the user's hand will inadvertently touch the shutter 7 during use, and this makes the device more convenient to use.

Since opening drive is performed by a sensor ejection mechanism, during ejection of the sensor 19 the shutter 7 is opened up, and the sensor 19 can be ejected outside of the main body case 1 through the sensor insertion opening 5, and this also makes the device more convenient to use. An example of this sensor ejection mechanism corresponds to the ejection manipulation component 6, the levers 21 and 21*a*, the linking component that links the lever 21 and the ejection manipulation component 6, and so forth in this embodiment.

The opening and closing plate 10 is biased by the spring 11 in the direction of closing the sensor insertion opening 5, so after the sensor 19 has been removed, the sensor insertion opening 5 automatically closes, preventing dust or the like from coming in. Thus, there is no need for the user to consciously close the shutter, which makes the device more convenient to use.

Since the sensor 19 is pressed upward by the opening and closing component 13 in its inserted state, it is less likely that the sensor 19 will accidentally fall out of the main body case 1.

Since the sensor 19 is also pressed upward by the opening and closing component 13 when the sensor 19 is separated from the connection terminal 20 in the course of ejecting the sensor 19 from the main body case 1, it is less likely that the elastic force of the connection terminal 20 will cause the opening and closing plate 10 to suddenly fly out of the sensor insertion opening 5.

Furthermore, since the above-mentioned pressing by the sensor ejection mechanism is released in the ejection of the sensor 19 from the main body case 1, the sensor 19 can smoothly ejected from the main body case 1.

Because the opening and closing component 13 has the inclined face 13a that is inclined inward from the sensor insertion opening 5, the opening and closing component 13 comes into contact with the sensor 19 and smoothly rotates when the sensor 19 is inserted, allowing the sensor insertion opening 5 to be opened up. In particular, in this embodiment the inclined face 13a is inclined so that its end on the outer peripheral side is positioned more on the rotation direction side of the rotation component 70 in the opening of the sensor insertion opening 5 than the end on the inner peripheral side, as viewed in the direction of the rotational axis 70a.

Because the dimension of the opening and closing plate 10 in the lateral direction is greater than the dimension of the sensor insertion opening 5 in the lateral direction, liquid that has spread out to the left and right of the opening and closing plate 10 through capillary action will be less likely to form drops and fall onto the connection terminal 20.

Because the coil spring component 11c is mounted to the outer periphery of the shaft component 8, liquid that has spread out along the closing components D and E will spread further outward along the capillary formed between the coils of the coil spring component 11c, which makes it less likely that the liquid will form drops and fall onto the connection terminal 20.

The spring 11 formed from metal results in better capillary action, and having the metal surface exposed results in even better capillary action.

Embodiment 2

Configuration of Biological Sample Measurement Device

Figure 20:
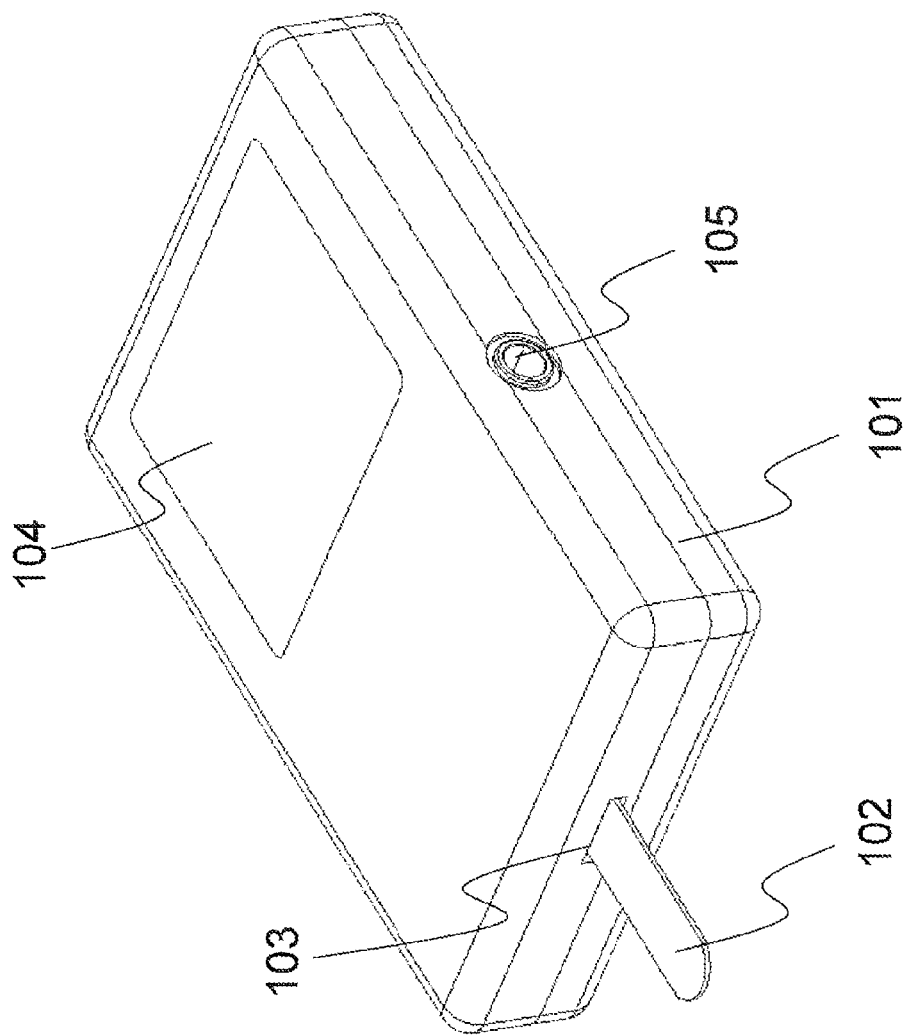
FIG. 20 is an oblique view of the biological sample measurement device in Embodiment 2 of the present invention.

In FIG. 20, 101 is a main body case with a cuboid shape. A sensor insertion opening 103 for inserting a sensor 102 is provided on the front face side of this main body case 101. A display component 104 for displaying the measured blood glucose level (an example of biological information) is provided on the upper face of this main body case 101.

With the main body case 101 in this Specification, the face of the main body case 101 where the display component 104 is provided is referred to as "above" (the upper side), the opposite side from the display component 104 is referred to as "below" (the lower side), the side on which the sensor insertion opening 103 is provided is referred to as the front (front side), and the opposite side the rear (rear side). The lateral direction shall be a direction that is perpendicular to the direction in which the sensor 102 is inserted, and a direction parallel to the upper face where the display unit 104 is provided.

Furthermore, a cylindrical jack 105 is provided as an example of a manipulation body insertion component to the side face of the main body case 101.

Figure 22:
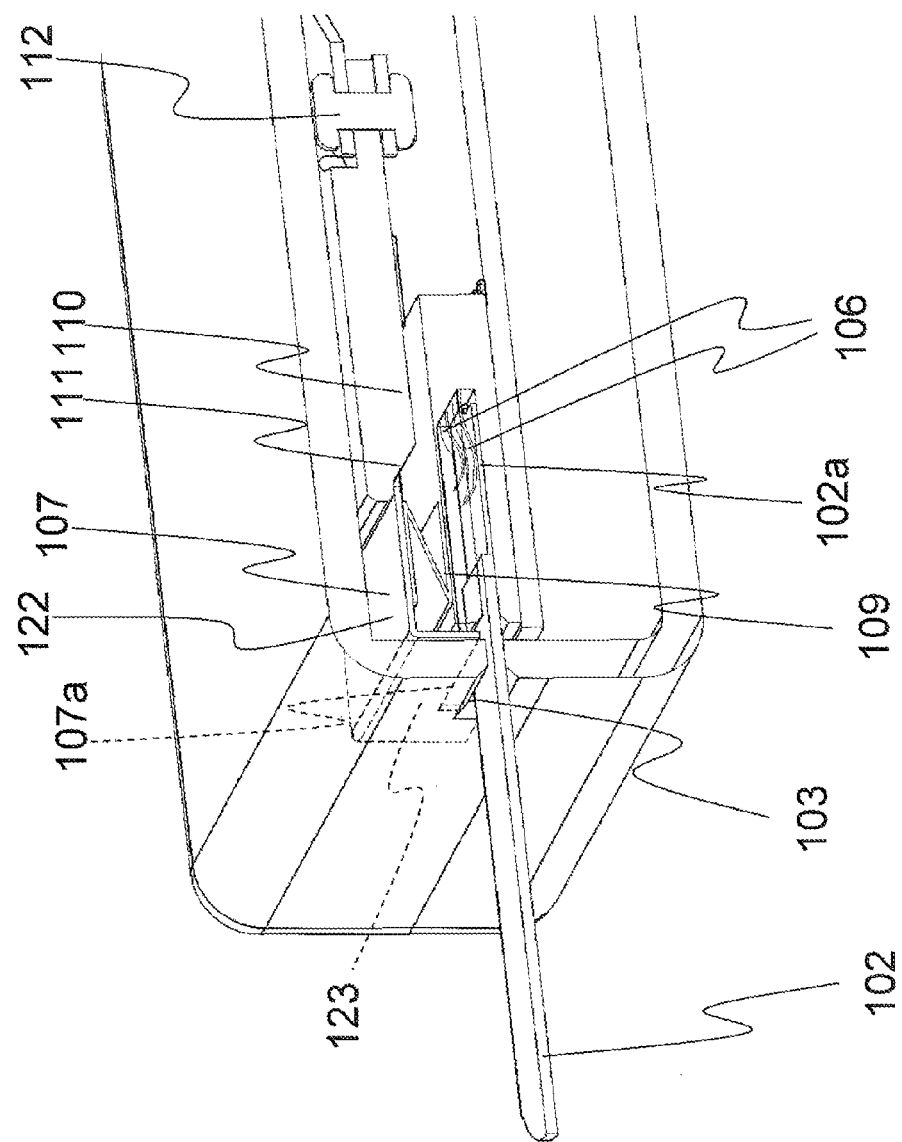
FIG. 22 is a detail see-through oblique view of the biological sample measurement device in Embodiment 2 of the present invention.
Figure 23:
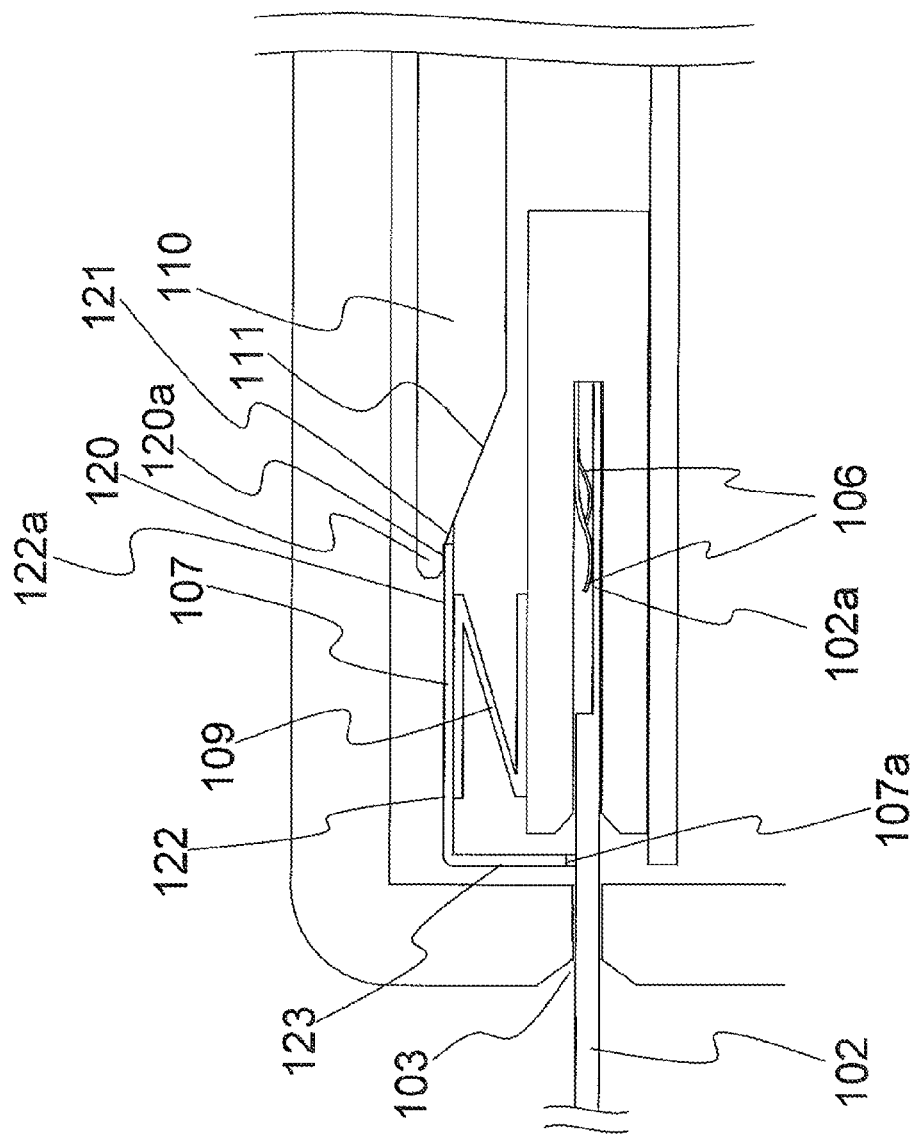
FIG. 23 is a detail cross section of the main components of the biological sample measurement device in Embodiment 2 of the present invention.

As shown in FIGS. 22 and 23, connection terminals 106 are provided behind the sensor insertion opening 103 inside the main body case 101, and a controller (not shown) is connected to these connection terminals 106.

Figure 21:
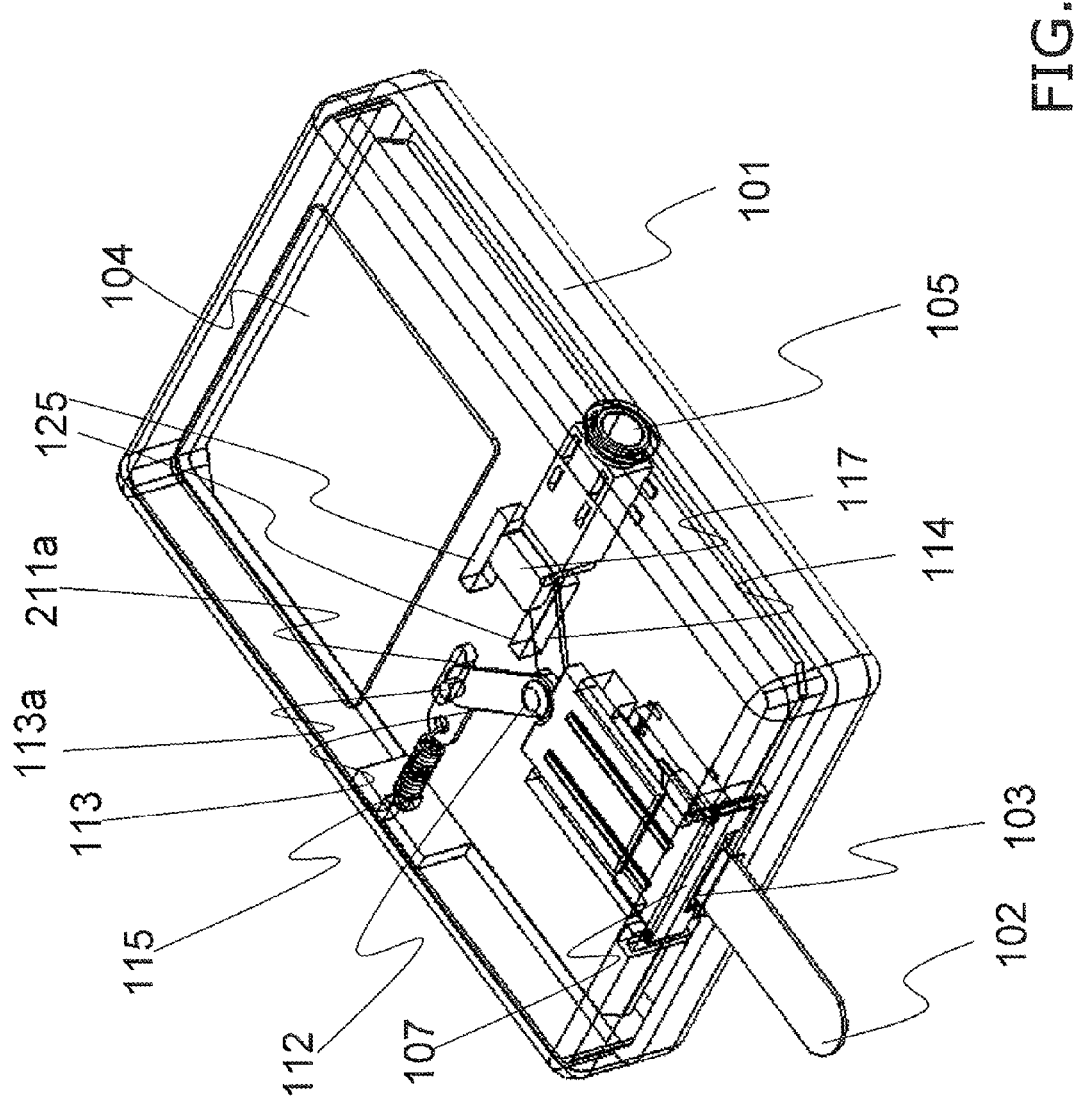
FIG. 21 is a see-through oblique view of the biological sample measurement device in Embodiment 2 of the present invention.

As shown in FIGS. 21 and 22, a shutter 107 that opens and closes the sensor insertion opening 103 is provided between the connection terminals 106 and the sensor insertion opening 103 inside the main body case 101.

Configuration of Shutter 107

Figure 26:
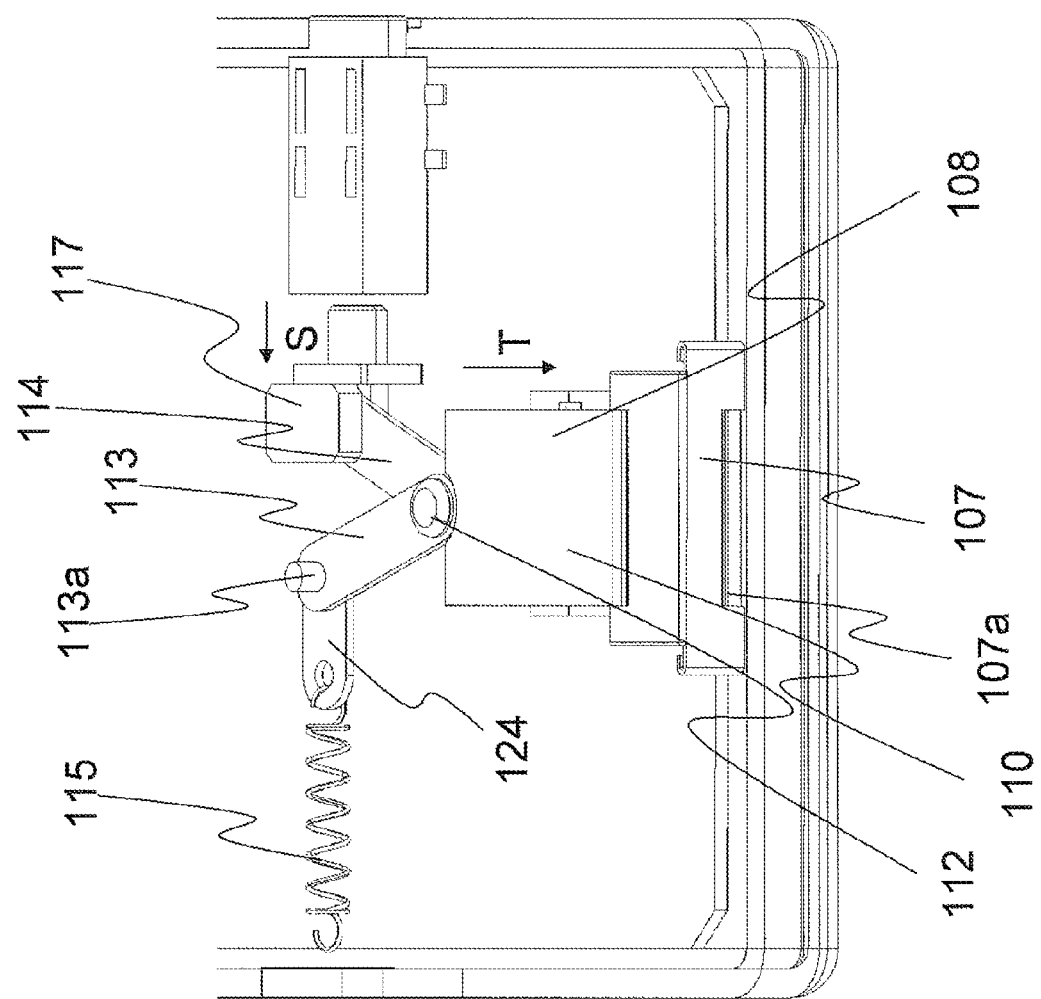
FIG. 26 is a see-through detail plan view of the biological sample measurement device in Embodiment 2 of the present invention.

As shown in FIGS. 22, 23, and 26, this shutter 107 is in the form of a flat member that has been bent in an approximate L shape in side view.

A concave component 107a that has the same shape as the sensor insertion opening 103 when the main body case 101 is seen from the front is provided. As shown in FIG. 22, when the sensor 102 is inserted into the sensor insertion opening 103, the sensor insertion opening 103 and the concave component 107a fit together, and as a result the sensor 102 can be inserted toward the connection terminals 106. An electrode component 102a is provided at one end of the sensor 102. When the sensor 102 is inserted from the electrode component 102a side into the main body case 101, the electrode component 102a is held down from above by the connection terminals 106. Because the electrode component 102a is thus held down from above by the connection terminals 106, the electrode component 102a and the connection terminals 106 are electrically connected, and the sensor 102 is held in the main body case 101.

Configuration of Shutter 107 and Shutter Drive Mechanism 108

As shown in FIGS. 21 to 26, a shutter drive mechanism 108 that opens and closes the shutter 107 is provided inside the main body case 101.

More specifically, as shown in FIG. 22, the shutter 107 is always biased upward by a leaf spring 109, and in this state, a driver 110 of the shutter drive mechanism 108 comes into contact with the rear end of the shutter 107. An inclined component 111 that is inclined upward from the rear toward the front is provided on the lower side at the distal end of the driver 110, and in a normal usage state, the upper end of the inclined component 111 is in contact with the rear end of the shutter 107.

As shown in FIG. 23, to describe this in further detail, the shutter 107, which is L-shaped in side view, has a support component 122 that is disposed substantially parallel to the insertion direction of the sensor 102 and is supported from below by the spring 109 (discussed below), and an opening and closing component 123 that is disposed facing downward from the front end of the support component 122. The driver 110 comes into contact with this support component 122. The above-mentioned concave component 107a is formed at the lower end part of the opening and closing component 123.

As shown in FIG. 23, a protrusion 120 that protrudes forward is formed at the upper end of the inclined component 111 on the distal side of the driver 110. In a normal usage state, when the upper face 122a of the support component 122 of the shutter 107 comes into contact with the lower face 120a of this protrusion 120, this restricts upward movement of the shutter 107 by the leaf spring 109. Also, an inclined component 121 that is inclined upward from the rear toward the front is provided at the upper side of the rear end of the support component 122 of the shutter 107, and the inclined component 111 comes into contact with this inclined component 121 from above. The term "normal usage state" refers to a state in which the measurement of blood glucose (an example of biological information) is carried out by inserting the sensor 102.

That is, in this state, as shown in FIGS. 22 and 23, the shutter 107 is biased upward by the leaf spring 109, and as a result, the concave component 107a of the shutter 107 and the sensor insertion opening 103 fit together, which allows the sensor 102 to be smoothly inserted into the connection terminals 106.

Figure 25:
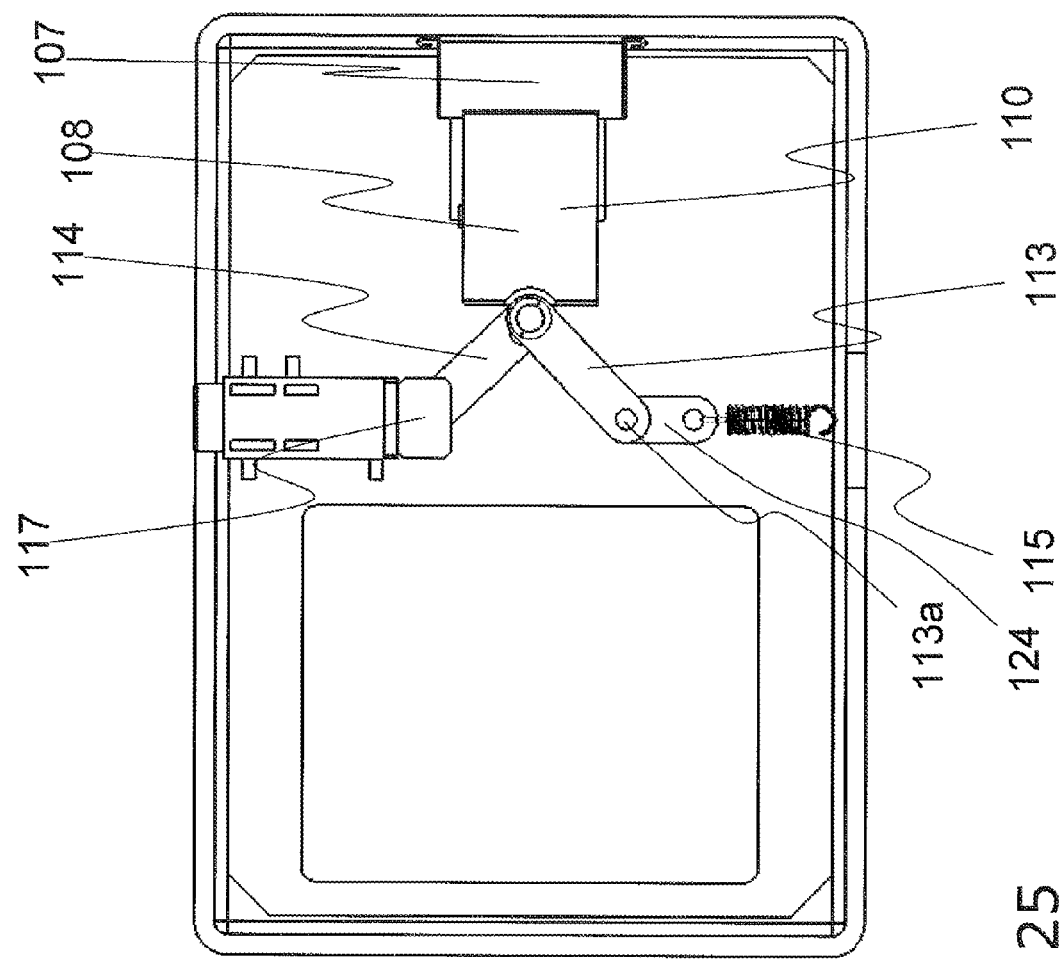
FIG. 25 is a see-through plan view of the biological sample measurement device in Embodiment 2 of the present invention.

As shown in FIGS. 21, 25, and 26, two levers 113 and 114 are linked via a shaft 112 to the rear end side of the driver 110. These two levers 113 and 114 are able to rotate around the shaft 112. Of the two, the rear end of the lever 113 is linked to a coil spring 115 via a linking member 124. This coil spring 115 corresponds to an example of a biasing body that biases the shutter 107 in the opening direction, and is linked at one end to the linking member 124, and is fixed at the other end to the inner peripheral face of the main body case 101. Also, a manipulated component 117 that is pushed in the inside direction of the main body case 101 by the external power transmission pin 116 is linked to the rear end of the lever 114 when the jack 105 is inserted into an external power transmission pin 116 (discussed below).

With this configuration, as shown in FIG. 26, the lever 113 and a protrusion 113a are pulled in the compression direction of the coil spring 115, and along with this, the distal end side of the driver 110 is pulled to the state in FIG. 22 (rearward) via the shaft 112. As a result, the sensor insertion opening 103 and the concave component 107a of the shutter 107 fit together as mentioned above. Consequently, the sensor 102 can be smoothly inserted into the connection terminals 106.

As shown in FIG. 21, the protrusion 113a is provided to the upper surface of the lever 113, for moving the coil spring 115 side of the lever 113 in a direction (lateral direction) that is perpendicular to the sensor insertion opening 103 and parallel to the upper face of the main body case 101, and the protrusion 113a is configured so as to move through a guide groove 211a provided to the main body case 101. Also, guide members 125 for guiding the manipulated component 117 in the lateral direction are provided on the front and rear sides of the manipulated component 117. The manipulated component 117 moves perpendicular with respect to the insertion direction of the sensor 102, and moves in a direction (lateral direction) that is parallel to the upper face of the main body case 101.

Operation of Biological Sample Measurement Device

Figure 24:
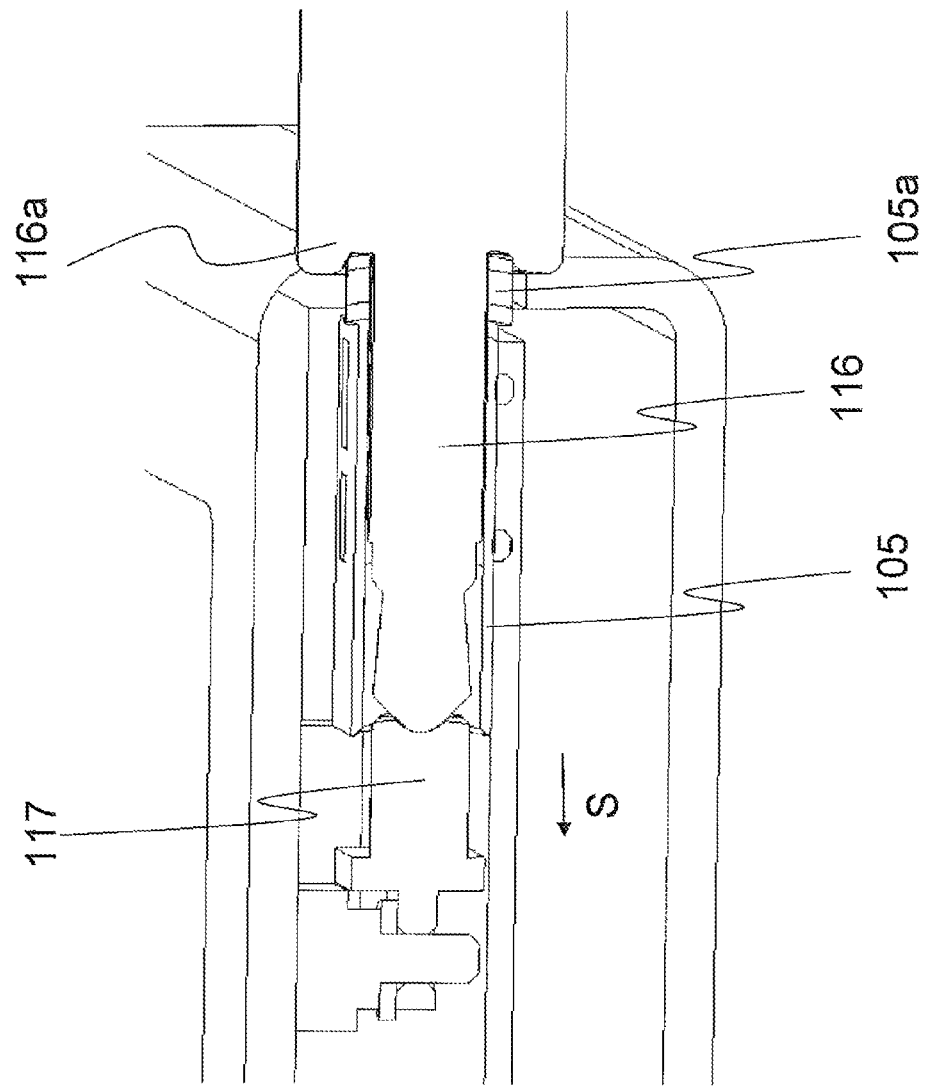
FIG. 24 is a detail cross section of the biological sample measurement device in Embodiment 2 of the present invention.

As shown in FIG. 24, the external power transmission pin 116 (an example of a manipulation body) for transmitting measurement data for this biological sample measurement device to the outside is inserted into the cylindrical jack 105 in this embodiment.

Since the measurement of blood glucose level by the sensor 102 is already finished at this point, the operation of inserting the external power transmission pin 116 into the jack 105 is performed in a state in which the sensor 102 has been taken out of the sensor insertion opening 103.

As shown in FIG. 24, when the external power transmission pin 116 (an example of a manipulation body) for transmitting measurement data for this biological sample measurement device to the outside is inserted into the jack 105, the distal end of the external power transmission pin 116 pushes on the manipulated component 117 linked to the lever 114 (see the arrow S). This pushed state is the state shown in FIG. 26 (the external power transmission pin 116 is not depicted in order to keep the drawing from being too complicated), and as a result, the lever 114 is pushed, and at the same time the driver 110 is pushed forward as shown in FIG. 26 (see the arrow T). At this point the coil spring 115 is extended.

Meanwhile, when the external power transmission pin 116 has been pulled out of the jack 105, and the biasing of the manipulated component 117 by the external power transmission pin 116 has been released, the driver 110 is pulled back by the biasing force of the coil spring 115.

Figure 27:
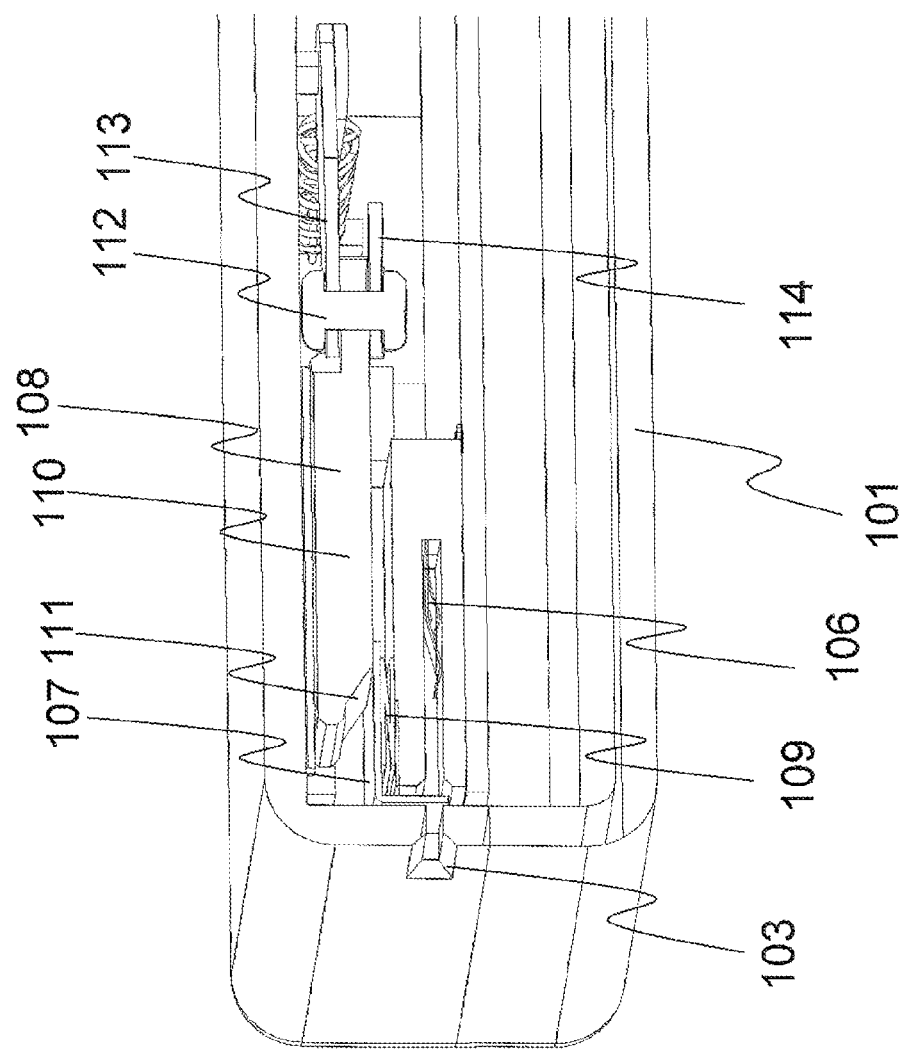
FIG. 27 is a detail cross section of the biological sample measurement device in Embodiment 2 of the present invention.

That is, since the inclined component 111 is provided to the distal end of the driver 110, and the inclined component 121 is provided to the rear end of the shutter 107, when the driver 110 is pushed forward, the inclined component 111 causes the shutter 107 to move downward while compressing the leaf spring 109. As a result, as shown in FIG. 27, the sensor insertion opening 103 is closed by the shutter 107. The stroke of the shutter 107 in the opening and closing direction (up and down) is determined by the amount of movement of the driver 110 in the longitudinal direction. Specifically, with a configuration such that the amount of forward movement of the driver 110 increases when the external power transmission pin 116 is inserted into the jack 105, there is more downward movement of the shutter 107, and the stroke in the opening and closing direction is longer.

Also, as shown in FIG. 24, the opening 105a of the jack 105 of the main body case 101 is covered by the external power transmission pin 116 in this state. Specifically, the opening 105a is covered by a portion 116a of the external power transmission pin 116 that is disposed outside the main body case 101 in an inserted state.

Action and Effect

In this embodiment, since the shutter 107 is provided between the connection terminals 106 and the sensor insertion opening 103 inside the main body case 101, when the sensor 102 is inserted into the sensor insertion opening 103, it is less likely that the user's hand will touch the shutter 107, and this facilitates sensor insertion and in turn makes the device more convenient to use.

Also, in this embodiment, since the jack 105 (an example of a manipulation body insertion component) is provided for inserting, from outside the main body case 101, the external power transmission pin 116 (an example of a manipulation body) that drives the shutter drive mechanism 108 provided inside the main body case 101, the job of closing the shutter 107 can be accomplished merely by inserting the external power transmission pin 116 (an example of a manipulation body) into the jack 105 (an example of a manipulation body insertion component), which makes the device more convenient to use in this respect as well.

Furthermore, in this embodiment, since the opening 105a of the jack 105 (an example of a manipulation body insertion component) outside the main body case 101 is covered by the portion 116a of the external power transmission pin 116 (an example of a manipulation body) inserted into this jack 105 (an example of a manipulation body insertion component) that is disposed on the outside of the main body case 101, not only the sensor insertion opening 103, but also the jack 105 (an example of a manipulation body insertion component) is covered. As a result, when the main body case 101 is washed with a disinfectant solution, it will be less likely that this disinfectant solution will find its way inside the main body case 101.

Other Embodiments

An embodiment of the present invention was described above, but the present invention is not limited to or by the above embodiment, and various modifications are possible without departing from the gist of the invention.

In Embodiment 1 above, as shown in FIG. 6, the manipulated component 12 was provided to the opening and closing plate 10, but need not be configured in this way, and may be provided to the shaft components 8 and 9, etc.

In Embodiment 2 above, the external power transmission pin 116 was given as an example of a manipulation body, but this is not limited to the external power transmission pin 116. Specifically, this can be any member that can push the manipulated component 117 and has no external power transmission function, but is preferably a member capable of covering the opening 105a. Also, a sealing member that seals the edges of the opening 105a may be provided to the portion of the manipulation body that covers the opening 105a. Providing a sealing member makes it less likely that disinfectant solution or the like will find its way in.

Also, in Embodiment 2, the inclined component 121 was formed at the rear end of the shutter 107, but need not be formed. However, it is preferable to form the inclined component 121 in order for the movement of the driver 110 and the shutter 107 to be smoother.

INDUSTRIAL APPLICABILITY

As discussed above, with this biological sample measurement device, it is easier to insert a sensor, which makes the device more convenient to use, so the device is expected to find use as a way to measure the blood glucose level and so forth of biological samples.

REFERENCE SIGNS LIST 1 main body case
2 upper case
3 lower case
4 display component
5 sensor insertion opening
6 ejection manipulation component
7 shutter
8 shaft component
9 shaft component
10 opening and closing plate
11 spring
11a engagement component
11b, 11d, 11f straight portion
11c coil spring component
11e engaged component
12 manipulated component
13 opening and closing component
13b contact component
14 shaft support
15 shaft support
16 protrusion
17 protrusion
18 engagement component
19 sensor
20 connection terminal
21 lever
21a lever
22 manipulation component
23 manipulation component
50 sensor insertion component
51 slit
70 rotation component
70a rotational axis
101 main body case
102 sensor
102a electrode component
103 sensor insertion opening
104 display component
105 jack
105a opening
106 connection terminal
107 shutter
108 shutter drive mechanism
109 leaf spring
110 driver
111 inclined component
112 shaft
113, 114 lever
113a protrusion
115 coil spring
116 external power transmission pin (an example of a manipulation body)
117 manipulated component
120 protrusion
121 inclined component
122 support component
123 opening and closing component
124 linking member
125 guide member

The invention claimed is:

1. A biological sample measurement device, comprising:
a main body case having a sensor insertion opening into which a sensor for measuring biological samples is inserted;
a connection terminal provided within the main body case and behind the sensor insertion opening;
a shutter that is provided within the main body case and between the sensor insertion opening and the connection terminal and that opens and closes the sensor insertion opening; and
a sensor ejection mechanism for ejecting the sensor mounted to the connection terminal to the outside of the main body case from the sensor insertion opening,
wherein the shutter is driven open by the sensor ejection mechanism during sensor ejection by the sensor ejection mechanism.

2. The biological sample measurement device according to claim 1,
wherein the shutter has:
a rotation component that is equipped with shaft components disposed on both sides of the sensor insertion opening, an opening and closing plate provided between the shaft components on both sides, and a manipulated component that is manipulated during opening drive by the sensor ejection mechanism, and that rotates around the shaft components by manipulation of the sensor ejection mechanism during sensor ejection by the sensor ejection mechanism; and a spring that biases the rotation component in the direction of closing the sensor insertion opening by the opening and closing plate.

3. The biological sample measurement device according to claim 2,
wherein the sensor insertion opening is formed wider than it is tall in the main body case, and
the width of the opening and closing plate in the lateral direction is greater than the width of the sensor insertion opening in the lateral direction.

4. The biological sample measurement device according to claim 2,
wherein the opening and closing plate has an opening and closing component disposed opposite the sensor insertion opening so as to block off the sensor insertion opening when the sensor insertion opening is closed, and
the manipulated component is provided on the opposite side of the opening and closing plate from the opening and closing component with respect to the shaft components.

5. The biological sample measurement device according to claim 4,
wherein the opening and closing component of the opening and closing plate has an inclined face that is inclined toward the inside of the sensor insertion opening.

6. The biological sample measurement device according to claim 2,
wherein the spring is a coil spring, and
the coil spring is mounted around the outer periphery of the shaft component of the shutter.

7. The biological sample measurement device according to claim 6,
wherein the opening and closing plate and the shaft components are formed from a synthetic resin, and
the coil spring is formed from metal.

8. The biological sample measurement device according to claim 7,
wherein a metal face appears at the surface of the coil spring.

9. The biological sample measurement device according to claim 6,
wherein shaft supports that support the shaft components of the shutter are provided on the outside of coil spring mounting components of the shaft components.

10. The biological sample measurement device according to claim 1, further comprising:
a shutter drive mechanism that is provided inside the main body case and that opens and closes the shutter; and
a manipulation body insertion component into which a manipulation body that drives the shutter drive mechanism is inserted from outside the main body case,
wherein the manipulation body insertion component has an opening formed in the surface of the main body case, and
the opening is covered by a portion of the manipulation body disposed outside the main body case when the manipulation body is inserted into the manipulation body insertion component.

11. The biological sample measurement device according to claim 10,
wherein the manipulation body insertion component is a cylindrical jack into which is inserted an external power transmission pin used as the manipulation body.

12. The biological sample measurement device according to claim 11,
wherein the shutter drive mechanism has a manipulated component that is manipulated by the manipulation body and is disposed behind the jack.

13. The biological sample measurement device according to claim 10,
wherein the shutter drive mechanism has a biasing body that biases the shutter in the direction of opening up the sensor insertion opening.

14. The biological sample measurement device according to claim 13,
wherein the biasing body is a coil spring.

15. The biological sample measurement device according to claim 14,
wherein the coil spring extends during manipulation of the shutter drive mechanism by the manipulation body.

16. The biological sample measurement device according to claim 13,
wherein the shutter drive mechanism has a driver that holds down the shutter in order to determine a stroke in the opening and closing direction of the shutter, and
the distal end side of the driver is formed in a shape that is inclined from below the main body case to above the main body case, and from the rear of the main body case toward the front of the main body case.

* * * * *